United States Patent
Wu et al.

(10) Patent No.: US 8,258,319 B2
(45) Date of Patent: Sep. 4, 2012

(54) EXO- AND DIASTEREO- SELECTIVE SYNTHESIS OF HIMBACINE ANALOGS

(75) Inventors: George G. Wu, Basking Ridge, NJ (US); Anantha Sudhakar, Fremont, CA (US); Tao Wang, Springfield, NJ (US); Ji Xie, Edison, NJ (US); Frank X. Chen, Plainsboro, NJ (US); Marc Poirier, Stewartsville, NJ (US); Mingsheng Huang, Plainsboro, NJ (US); Vijay Sabesan, Millbrae, CA (US); Daw-long Kwok, Gillette, NJ (US); Jian Cui, Edison, NJ (US); Xiaojing Yang, Waterford, CT (US); Tiruvettipuram K. Thiruvengadam, Kendall Park, NJ (US); Jing Liao, Edison, NJ (US); Ilia Zavialov, Princeton, NJ (US); Hoa N. Nguyen, Dayton, NJ (US); Ngiap Kie. Lim, Somerset, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 13/168,029

(22) Filed: Jun. 24, 2011

(65) Prior Publication Data

US 2011/0251392 A1 Oct. 13, 2011

Related U.S. Application Data

(62) Division of application No. 12/505,079, filed on Jul. 17, 2009, now Pat. No. 7,989,653, which is a division of application No. 11/331,324, filed on Jan. 12, 2006, now Pat. No. 7,605,275.

(60) Provisional application No. 60/644,464, filed on Jan. 14, 2005.

(51) Int. Cl.
C07D 307/92 (2006.01)
(52) U.S. Cl. ........................................ 549/299
(58) Field of Classification Search ................ 549/299
See application file for complete search history.

(56) References Cited

U.S. PATENT DOCUMENTS

| | | | |
|---|---|---|---|
| 6,063,847 A | 5/2000 | Chackalamannil et al. |
| 6,326,380 B1 | 12/2001 | Chackalamannil et al. |
| 6,645,987 B2 | 11/2003 | Chackalamannil et al. |
| 7,235,567 B2 | 6/2007 | Wu |
| 7,304,078 B2 | 12/2007 | Chackalamannil et al. |

FOREIGN PATENT DOCUMENTS
WO WO 03/089428 A1 10/2003

OTHER PUBLICATIONS

International Search Report dated Aug. 7, 2006 for corresponding PCT Application No. PCT/US2006/000954—6 Pages.
Chackalamannil, S., et al., "Discovery of Potent Orally Active Thrombin Receptor (Protease Activated Receptor 1) . . . ", J. Med. Chem, Sep. 22, 2005; vol. 48, No. 19, pp. 5884-5887.
Clasby, M.C., et al., "Discovery & Synthesis of a novel series of quinoline-based thrombin receptor . . . ", Bioorganic and Medicinal Letters; Mar. 15, 2006, vol. 16, No. 6, pp. 1548.
Hatayama, K., et al., "Production of optically active propargyl alcohol derivs.-e.g. alkoxy-hydroxy-butyne or derive . . . "; Derwent; Abstract; 1996-040245; 2pgs.
Tao, Beata, et al. "Nonenzymatic Kinetic Resolution of Propargylic Alcohols by a Planar-Chiral . . . ", J. Am. Chem. Soc., 1999, 121, pp. 5091-5091, web published May 14, 1999.
Dorwald, "Side Reactions in Organic Synthesis", 2005, Wiley: VCH, Weinheim, Preface, p. 1-15 & Chapter 8, pp. 279-308.

*Primary Examiner* — Patricia Morris
(74) *Attorney, Agent, or Firm* — Mark W. Russell

(57) ABSTRACT

This application discloses a novel process for the preparation of himbacine analogs useful as thrombin receptor antagonists. The process is based in part on the use of a base-promoted dynamic epimerization of a chiral nitro center. The chemistry taught herein can be exemplified by the following:

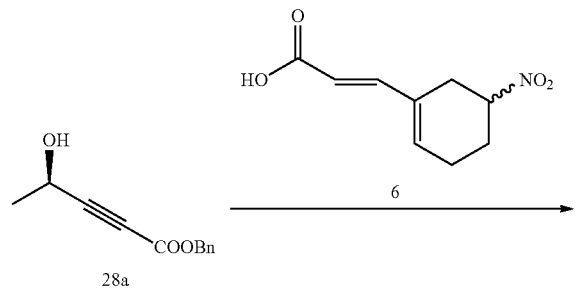

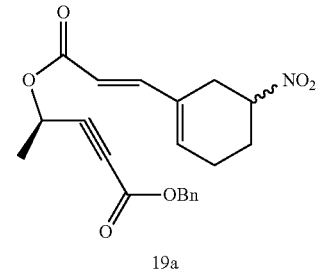

11 Claims, No Drawings

EXO- AND DIASTERO- SELECTIVE SYNTHESIS OF HIMBACINE ANALOGS

CROSS-REFERENCE TO RELATED APPLICATIONS

This application is a divisional application of application U.S. Ser. No. 12/505,079, which was filed Jul. 17, 2009 and is now U.S. Pat. No. 7,989,653, which in turn is a divisional application of application U.S. Ser. No. 11/331,324, which was filed on Jan. 12, 2006 and matured into U.S. Pat. No. 7,605,275 B1, which in turn claimed benefit of provisional application U.S. Ser. No. 60/644,464, filed on Jan. 14, 2005, all herein incorporated by reference.

FIELD OF THE INVENTION

This application discloses a novel process for the preparation of himbacine analogs useful as thrombin receptor antagonists. The process is based in part on the use of a base-promoted dynamic epimerization of a chiral nitro center. The invention disclosed herein is related to those disclosed in co-pending patent applications corresponding to the following provisional patent applications: Ser. No. 60/643,932; Ser. No. 60/643,927; and, Ser. No. 60/644,428, all four applications having been filed on the same date.

BACKGROUND OF THE INVENTION

Thrombin is known to have a variety of activities in different cell types and thrombin receptors are known to be present in such cell types as human platelets, vascular smooth muscle cells, endothelial cells, and fibroblasts. Thrombin receptor antagonists may be useful in the treatment of thrombotic, inflammatory, atherosclerotic and fibroproliferative disorders, as well as other disorders in which thrombin and its receptor play a pathological role. See, for example, U.S. Pat. No. 6,063,847, the disclosure of which is incorporated by reference.

One thrombin receptor antagonist is a compound of the formula:

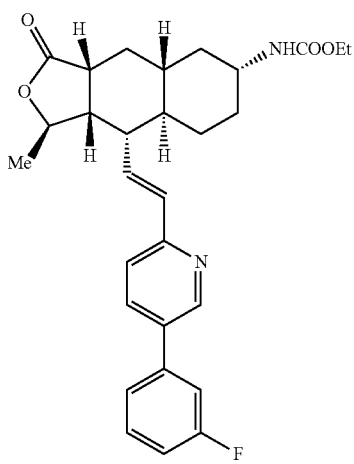

This compound is an orally bioavailable thrombin receptor antagonist derived from himbacine. Compound 11 may be synthesized from Compound 1:

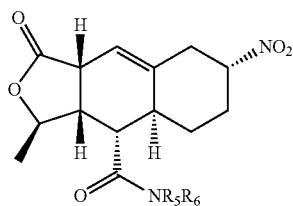

wherein $R_5$ and $R_6$ are each independently selected from the group consisting of H, alkyl, alkenyl, alkynyl, alkoxy, cycloalkyl, aryl, alkylaryl, arylalkyl, and heteroaryl groups.

Processes for the synthesis of similar himbacine analog thrombin receptor antagonists are disclosed in U.S. Pat. No. 6,063,847, and U.S. publication no. 2003/0216437, methods of using thrombin receptor antagonists are disclosed in U.S. publication no. 2004/0192753, and the synthesis of the bisulfate salt of a particular himbacine analog is disclosed in U.S. publication no. 2004/0176418, now U.S. Pat. No. 7,235,567, the disclosures of which are incorporated by reference herein. The present application provides a novel process for preparing Compound 11 from Compound 1, which process provides an improved yield and the elimination of the need for a chiral intermediate.

SUMMARY OF THE INVENTION

One aspect of the present invention provides a process for preparing Compound 1:

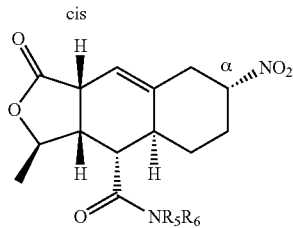

said process comprising the steps of:
(a) cyclizing Compound 2 in a first solvent at an elevated temperature

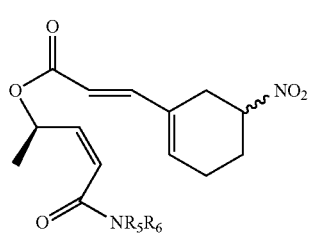

wherein $R_5$ and $R_6$ are each independently selected from the group consisting of H, alkyl, alkenyl, alkynyl, alkoxy, cycloalkyl, aryl, alkylaryl, arylalkyl, heterocyclic and heteroaryl groups, or $R_5$ and $R_6$, together with the nitrogen to which they are attached, form a 3- to 6-membered heterocyclic compound containing 1-4 heteroatoms, to produce a first mixture of exo isomers

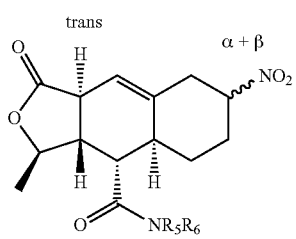

said isomers having a trans-[5,6]-ring-junction and endo isomers:

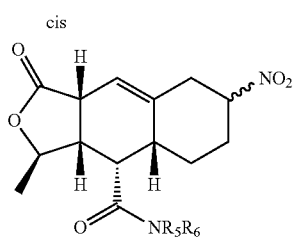

(b) epimerizing said trans-[5,6]-ring-junction in Compound 29 by treating said first mixture with a first base to produce a second mixture comprising cis-[5,6]ring-junction-nitro-α isomer and cis-[5,6]-ring-junction-nitro-β isomer of Compound 30:

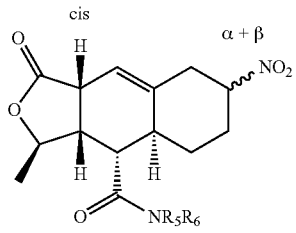

and (c) treating said second mixture with a second solvent, causing said α-isomer of Compound 30 to precipitate to produce Compound 1.

In another embodiment, the above process further comprises the step of treating said second mixture with a second base, resulting in a dynamic resolution of said second mixture, in which said β-isomer of Compound 30 is converted to α-isomer of Compound 30, and α-isomer of Compound 30 is precipitated to produce Compound 1.

In another embodiment, said first solvent is selected from the group consisting of xylene, N-methylpyrrolidinone, Dimethylsulfoxide, diphenyl ether, Dimethylacetamide, and mixtures of 2 or more thereof.

In another embodiment, said temperature is between about 70 and about 190° C., preferably between about 80 and about 170° C., more preferably between about 100 and about 160° C., still more preferably between about 120 and about 150° C.

In another embodiment, said first base is selected from the group consisting of triethylamine, 1,5-diazabicyclo[4,3,0]non-5-ene 1,4-diazabicyclo[2,2,2]octane, and 1,8-diazabicyclo[5,4,0]undec-7-ene, and mixtures of 2 or more thereof.

In another embodiment, said second solvent is selected from the group consisting of alcohols, ethers, ketones, esters, xylene, N-methylpyrrolidinone, and mixtures of 2 or more thereof.

In another embodiment, the invention provides a process for preparing Compound 2:

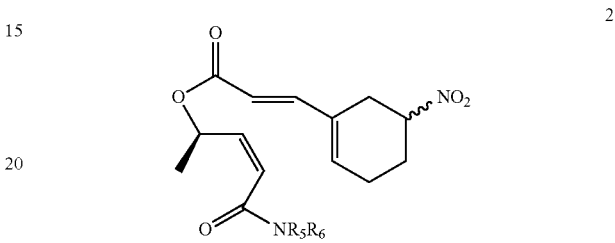

wherein $R_5$ and $R_6$ are each independently selected from the group consisting of H, alkyl, alkenyl, alkynyl, alkoxy, cycloalkyl, aryl, alkylaryl, arylalkyl, heterocyclic and heteroaryl groups, or $R_5$ and $R_6$, together with the nitrogen to which they are attached, form a 3- to 6-membered heterocyclic compound containing 1-4 heteroatoms, said process comprising:

(a) converting (R)-butynol to Compound 3:

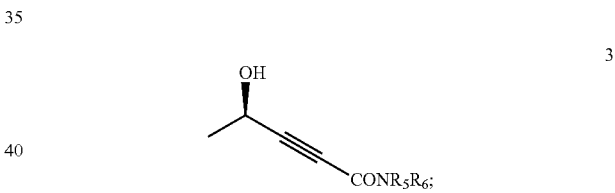

(b) reducing Compound 3 to yield Compound 4:

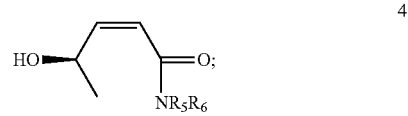

and, (c) reacting Compound 4 with Compound 6:

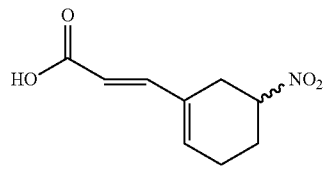

to yield Compound 2.

In yet another embodiment, the invention is directed to a process for preparing Compound 2:

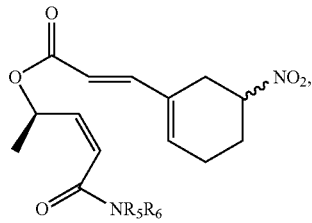
2 wherein $R_5$ and $R_6$ are each independently selected from the group consisting of H, alkyl, alkenyl, alkynyl, alkoxy, cycloalkyl, aryl, alkylaryl, arylalkyl, heterocyclic and heteroaryl groups, or $R_5$ and $R_6$, together with the nitrogen to which they are attached, form a 3- to 6-membered heterocyclic compound containing 1-4 heteroatoms, said process comprising:

(a) converting (R)-butynol to Compound 3:

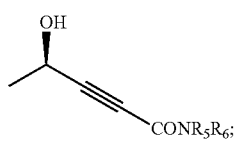
3

(b) reacting Compound 3 with Compound 6 to yield Compound 7:

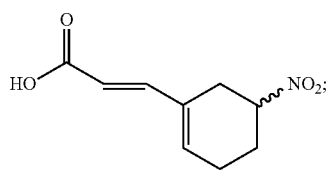
6

(c) reducing Compound 7 to produce Compound 2:

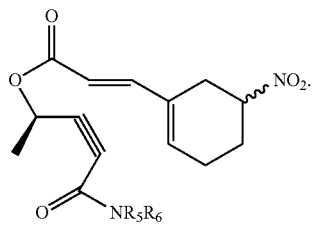
7

In another embodiment, the invention provides the following compounds:

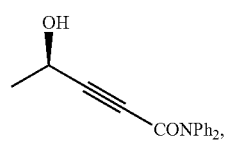
3a

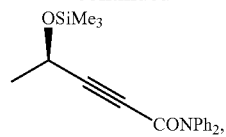

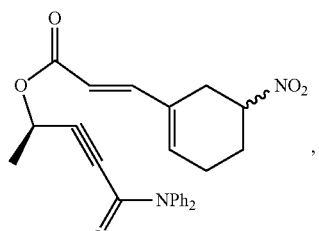
7a

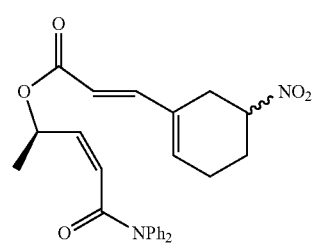
2

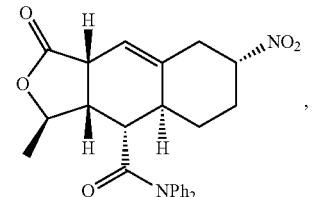
1a

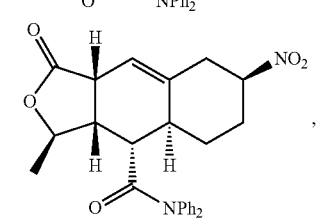

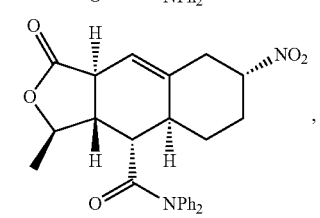

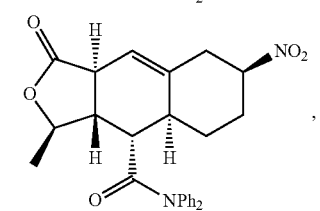

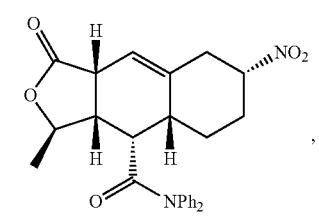

-continued
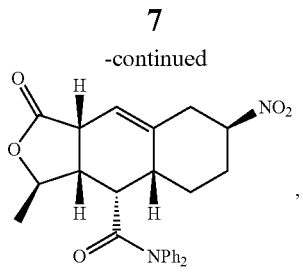
5
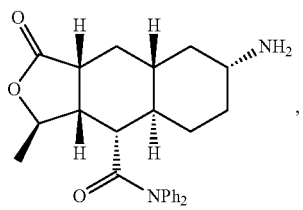
12a
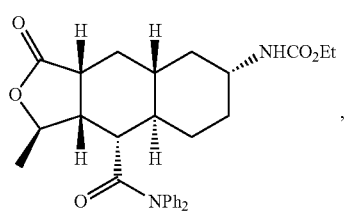
13a
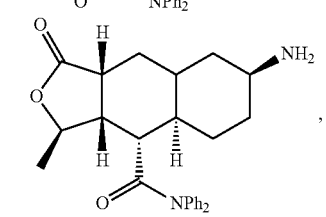
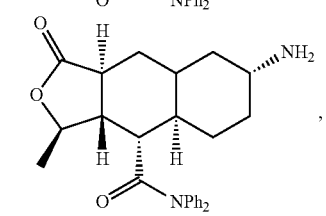
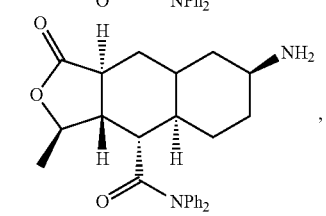
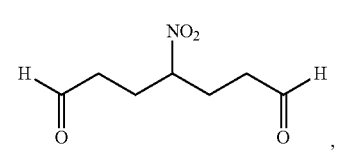
8
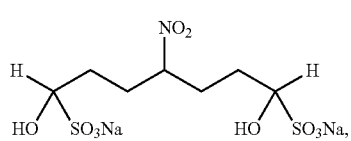
9
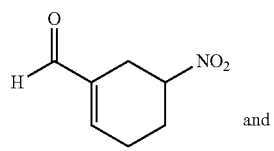
10
and
-continued
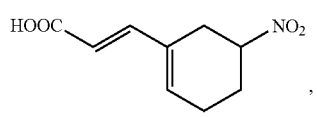
6
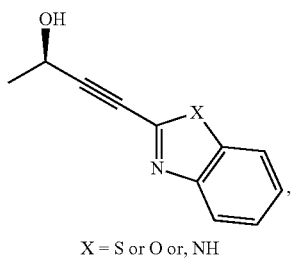
23
X = S or O or, NH
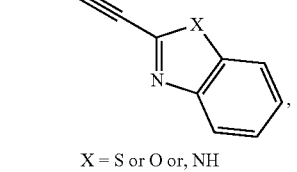
25
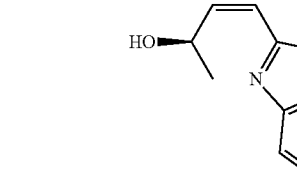
24
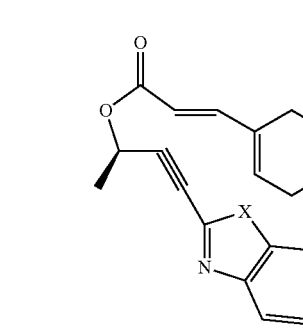
22
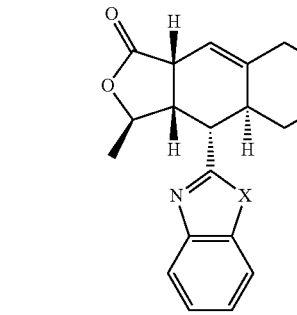
21

9
-continued

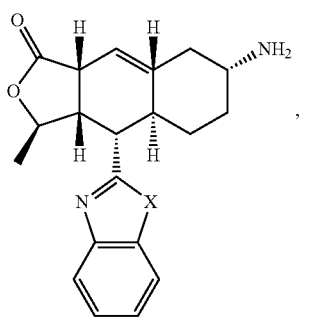

26

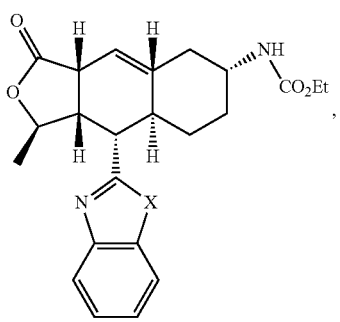

27

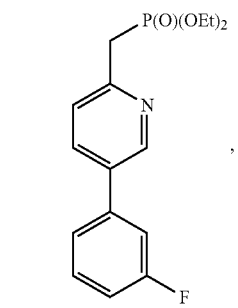

28

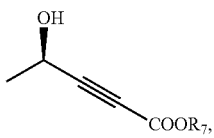

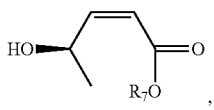

19

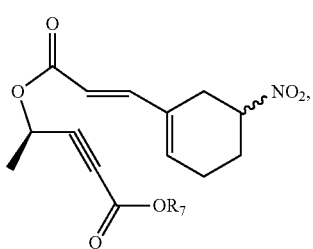

10
-continued

18

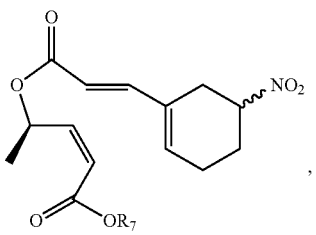

17

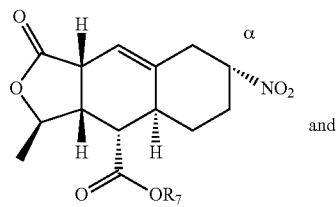

and

20

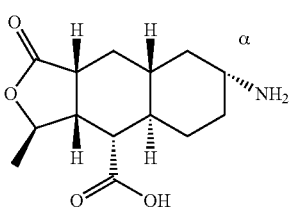

16

A further understanding of the invention will be had from the following detailed description of the invention.

DESCRIPTION OF THE INVENTION

The following definitions and terms are used herein or are otherwise known to a skilled artisan. Except where stated otherwise, the definitions apply throughout the specification and claims. Chemical names, common names and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Unless otherwise known, stated or shown to be to the contrary, the point of attachment for a multiple term substituent (two or more terms that are combined to identify a single moiety) to a subject structure is through the last named term of the multiple term substituent. For example, a cycloalkylalkyl substituent attaches to a targeted structure through the latter "alkyl" portion of the substituent (e.g., structure-alkyl-cycloalkyl).

The identity of each variable appearing more than once in a formula may be independently selected from the definition for that variable, unless otherwise indicated.

Unless stated, shown or otherwise known to be the contrary, all atoms illustrated in chemical formulas for covalent compounds possess normal valencies. Thus, hydrogen atoms, double bonds, triple bonds and ring structures need not be expressly depicted in a general chemical formula.

Double bonds, where appropriate, may be represented by the presence of parentheses around an atom in a chemical formula. For example, a carbonyl functionality, —CO—, may also be represented in a chemical formula by —C(O)—, or —C(=O)—. One skilled in the art will be able to determine the presence or absence of double (and triple bonds) in a covalently-bonded molecule. For instance, it is readily recognized that a carboxyl functionality may be represented by —COON, —C(O)OH, —C(=O)OH or —CO$_2$H.

The term "heteroatom," as used herein, means a nitrogen, sulfur or oxygen atom. Multiple heteroatoms in the same group may be the same or different.

As used herein, the term "alkyl" means an aliphatic hydrocarbon group that can be straight or branched and comprises 1 to about 24 carbon atoms in the chain. Preferred alkyl groups comprise 1 to about 15 carbon atoms in the chain. More preferred alkyl groups comprise 1 to about 6 carbon atoms in the chain. "Lower alkyl" means alkyl groups of 1 to 6 carbon atoms in the chain. "Branched" means that one or more lower alkyl groups such as methyl, ethyl or propyl, are attached to a linear alkyl chain. The alkyl can be substituted by one or more substituents independently selected from the group consisting of halo, aryl, cycloalkyl, cyano, hydroxy, alkoxy, alkylthio, amino, —NH(alkyl), —NH(cycloalkyl), —N(alkyl)$_2$ (which alkyls can be the same or different), carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkoxy" means an alkyl-O— group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen.

The term "cycloalkyl" as used herein, means an unsubstituted or substituted, saturated, stable, non-aromatic, chemically-feasible carbocyclic ring having preferably from three to fifteen carbon atoms, more preferably, from three to eight carbon atoms. The cycloalkyl carbon ring radical is saturated and may be fused, for example, benzofused, with one to two cycloalkyl, aromatic, heterocyclic or heteroaromatic rings. The cycloalkyl may be attached at any endocyclic carbon atom that results in a stable structure. Preferred carbocyclic rings have from five to six carbons. Examples of cycloalkyl radicals include cyclopropyl, cyclobutyl, cyclopentyl, cyclohexyl, cycloheptyl, or the like.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 10 carbon atoms in the chain; and more preferably about 2 to about 6 carbon atoms in the chain. Branched means that one or more lower alkyl groups such as methyl, ethyl or propyl, are attached to a linear alkynyl chain. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, aryl and cycloalkyl.

The term "aryl," as used herein, means a substituted or unsubstituted, aromatic, mono- or bicyclic, chemically-feasible carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, tolyl, xylyl, cumenyl, naphthyl, tetrahydronaphthyl, indanyl, indenyl, or the like. If desired, the carbocyclic moiety can be substituted with from one to five, preferably, one to three, moieties, such as mono- through pentahalo, alkyl, trifluoromethyl, phenyl, hydroxy, alkoxy, phenoxy, amino, monoalkylamino, dialkylamino, or the like.

"Heteroaryl" means a monocyclic or multicyclic aromatic ring system of about 5 to about 14 ring atoms, preferably about 5 to about 10 ring atoms, in which one or more of the atoms in the ring system is/are atoms other than carbon, for example nitrogen, oxygen or sulfur. Mono- and polycyclic (e.g., bicyclic) heteroaryl groups can be unsubstituted or substituted with a plurality of substituents, preferably, one to five substituents, more preferably, one, two or three substituents (e.g., mono- through pentahalo, alkyl, trifluoromethyl, phenyl, hydroxy, alkoxy, phenoxy, amino, monoalkylamino, dialkylamino, or the like). Typically, a heteroaryl group represents a chemically-feasible cyclic group of five or six atoms, or a chemically-feasible bicyclic group of nine or ten atoms, at least one of which is carbon, and having at least one oxygen, sulfur or nitrogen atom interrupting a carbocyclic ring having a sufficient number of pi ($\pi$) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "heterocyclic ring" or "heterocycle," as used herein, means an unsubstituted or substituted, saturated, unsaturated or aromatic, chemically-feasible ring, comprised of carbon atoms and one or more heteroatoms in the ring. Heterocyclic rings may be monocyclic or polycyclic. Monocyclic rings preferably contain from three to eight atoms in the ring structure, more preferably, five to seven atoms. Polycyclic ring systems consisting of two rings preferably contain from six to sixteen atoms, most preferably, ten to twelve atoms. Polycyclic ring systems consisting of three rings contain preferably from thirteen to seventeen atoms, more preferably, fourteen or fifteen atoms. Each heterocyclic ring has at least one heteroatom. Unless otherwise stated, the heteroatoms may each be independently selected from the group consisting of nitrogen, sulfur and oxygen atoms.

The terms "Hal," "halo," "halogen" and "halide," as used herein, mean a chloro, bromo, fluoro or iodo atom radical. Chlorides, bromides and fluorides are preferred halides.

The term "carbonate", as used herein, is understood to include bicarbonates.

The term "isomer", as used herein, is understood to mean one of two or more molecules having the same number and kind of atoms and hence the same molecular weight, but differing in respect to the arrangement or configuration of the atoms.

The term "epimerizing", as used herein, is understood to mean converting from one isomer to another, wherein it is the relative position of an attached H that differs between the two isomers.

The term "precipitate", as used herein, is understood to mean to fall out of solution as a solid.

The term "dynamic resolution", as used herein, is understood to mean a process in which a conversion from a first isomer to a second isomer of the same compound in a solution is thermodynamically driven by the depletion of the second isomer from the solution by precipitation of the second isomer.

The following abbreviations are defined: EtOH is ethanol; Me is methyl; Et is ethyl; Bu is butyl; n-Bu is normal-butyl, t-Bu is Cert-butyl, OAc is acetate; KOt-Bu is potassium Cert-butoxide; NBS is N-bromo succinimide; NMP is 1-methyl-2-pyrrolidinone; DMAP is 4-dimethylaminopyridine; THF is tetrahydrofuran; DBU is 1,8-diazabicyclo[5,4,0]undec-7-ene; DMA is N,N-dimethylacetamide; n-Bu$_4$NBr is tetrabutylammonium bromide; n-Bu$_4$NOH is tetrabutylammonium hydroxide, n-Bu$_4$N(HSO$_4$) is tetrabutylammonium hydrogen sulfate, and "equiv." or "eq." means equivalents.

"n", as it is used herein, is understood to be an integer having a value that is inclusive of the range recited thereafter. Thus "n is between 0 and 4" and "n ranges 0-4" both mean that n may have any of the values 0, 1, 2, 3 or 4.

General Syntheses

The following scheme summarizes the dynamic resolution-based approach to synthesizing Compound 11 from (R)-butynol:

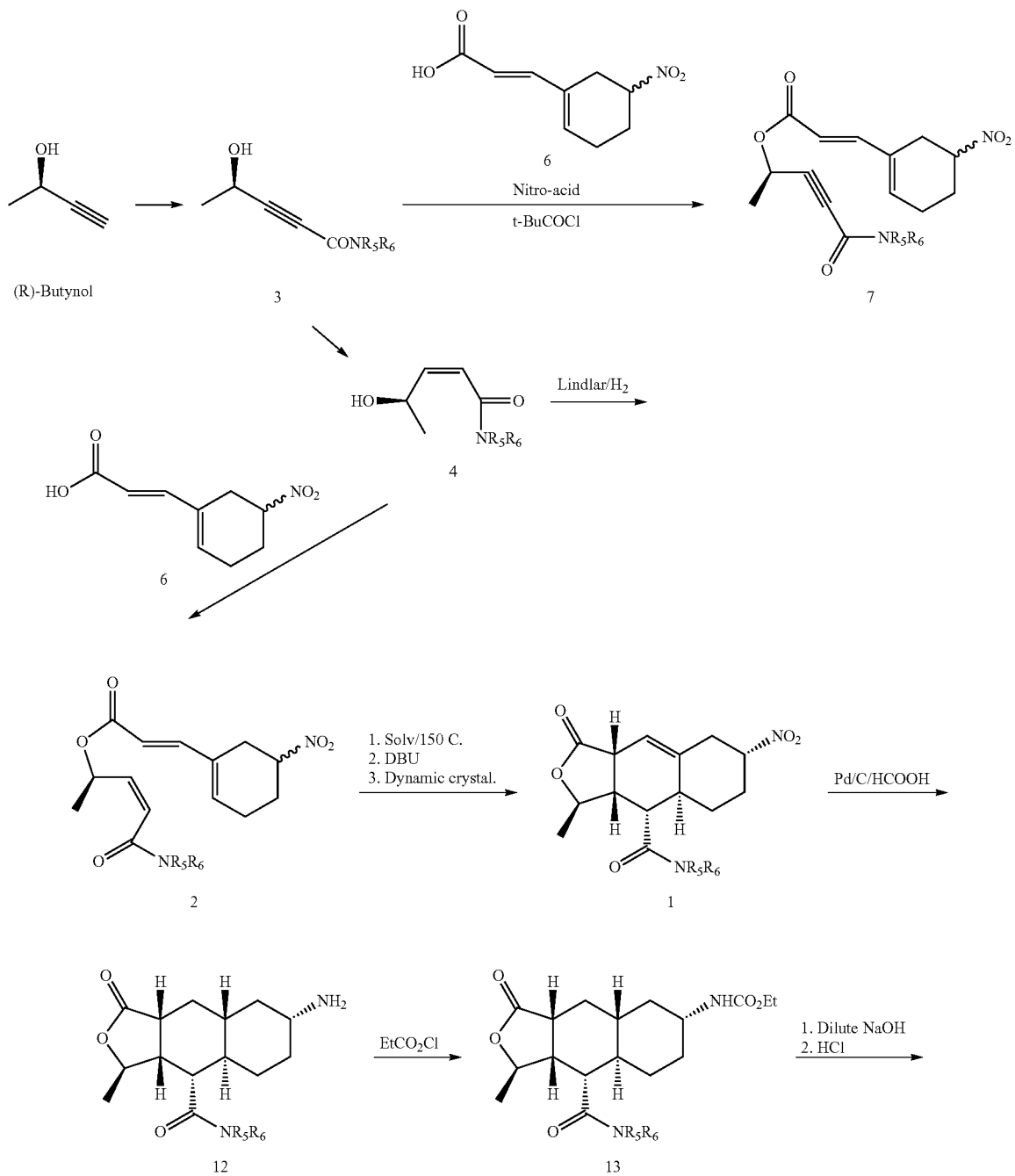

-continued
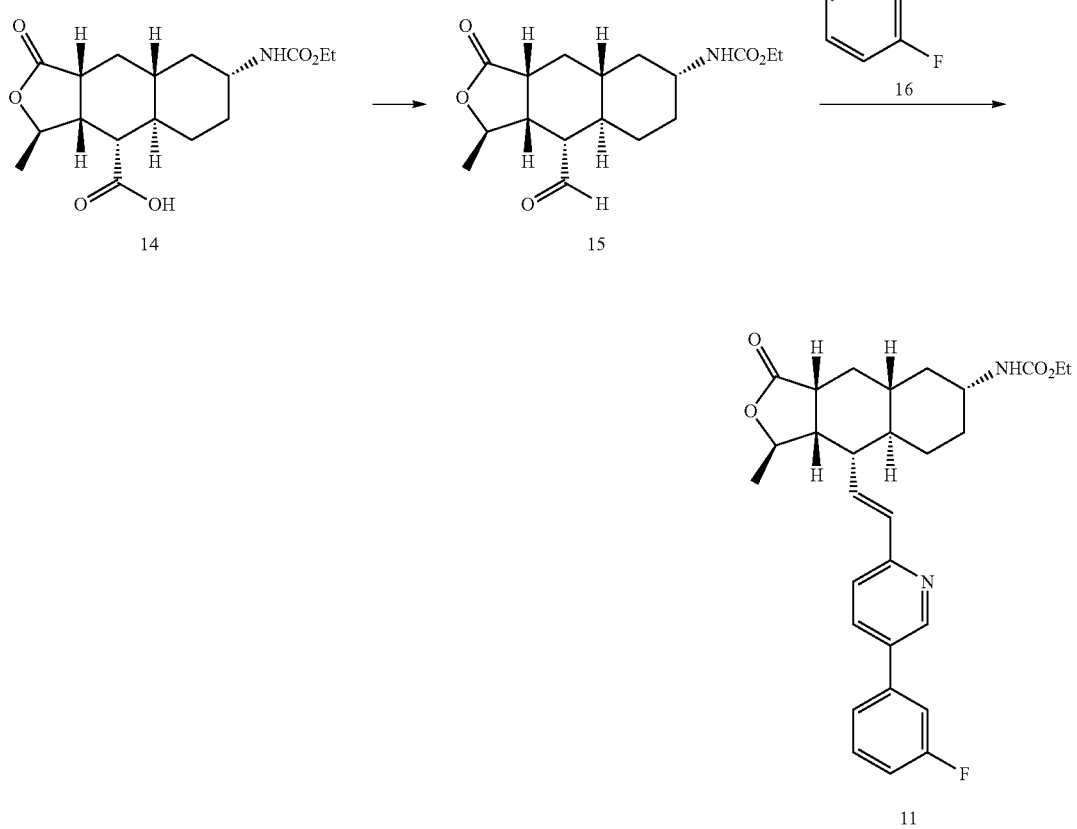
(R)-butynol may be converted to amide 3 by either of Methods A or B:
Preparation of Amide-Method A:
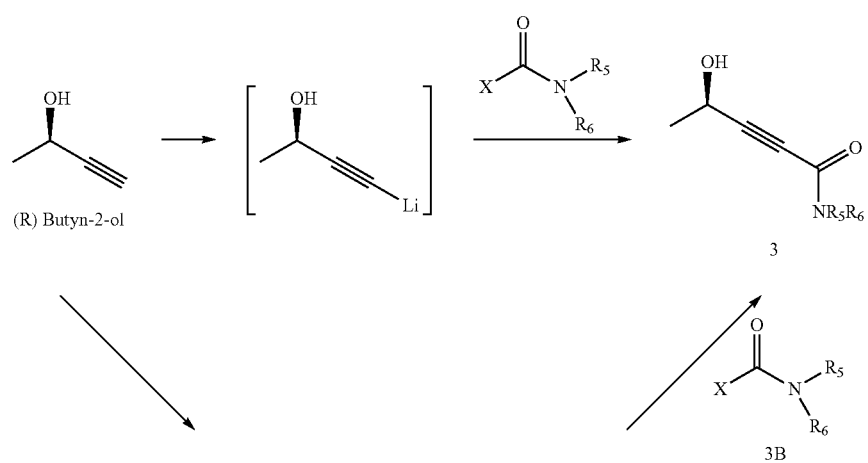

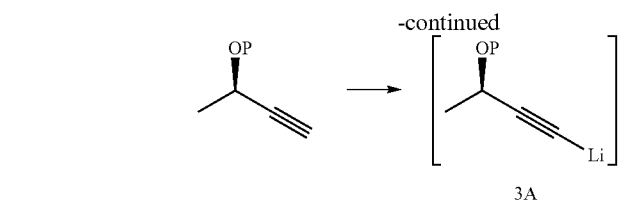

3A

P = protecting group such as THP, SiR¹R²R³

Preparation of Amide-Method B:

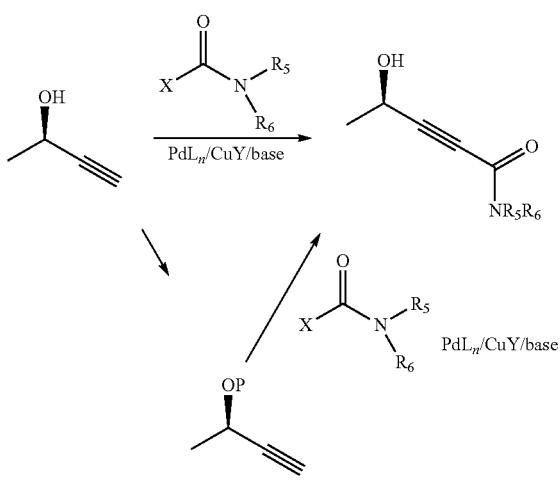

In each of methods A and B, P is a protecting group, for example THP or SiR¹R²R³, wherein R¹-R³ may be H, alkyl, alkenyl, cycloalkyl, aryl, arylalkyl, alkylaryl, heterocyclic, and heteroaryl groups, Y is selected from the group consisting of Cl, Br, I, and R'''COO, wherein R''' is selected from the group consisting of alkyl, aryl, alkylaryl, and arylalkyl and X is a leaving group. By way of example, X can be halogen, for example Cl, Br, or I. As another example, X can be selected from heterocyclic rings, such as imidazoles. L is a ligand and is selected from PR' wherein R' is selected from alkyl, aryl, alkylaryl, and NR'' groups, and R'' is selected from alkyl, aryl, and alkylaryl groups. n can range from 0-8, and preferably ranges from 0 to 4.

The butyn-2-ol is disclosed in, e.g., U.S. Pat. No. 6,063,847, and Methods A and B may be performed on either the racemic or enantiopure butynol. The butynol may be combined with a mineral acid, for example sulfuric acid, in an organic solvent such as THF and a compound such as hexyldimethylsilazane to provide a protecting group on the alcohol. The protected compound may then be combined with a suitable base. A preferred nucleophilic base is hexyllithium. The resulting metallated compound may then be amidated by combining it with a solution containing, e.g., diphenylcarbamylimidazole, and deprotected, to yield the diphenylamide (Compound 3 wherein $R_5$ and $R_6$ are both phenyl).

The amide may then be converted to Compound 2 via either of two routes: through vinyl alcohol 4, or through amide 7. For example, amide 3 may be combined with nitro acid 6. In one embodiment, amide 3 reacts with a mixed anhydride of the nitro acid 6 (prepared from 6 and pivaloyl chloride in the presence of a tert-amine base), in the presence of DMAP to form Compound 7. The amide is subsequently subjected to hydrogenation conditions to yield Compound 2. Preferred hydrogenation conditions include pressurized hydrogen in the presence of a hydrogenation catalyst. The hydrogen pressure may range from 20 to 500 psi, and a pressure of 100 psi is preferred. The hydrogenation catalyst may be a noble metal catalyst, for example Lindlar catalyst. The hydrogenation is suitably conducted in the presence of a solvent, preferably an aromatic solvent such as toluene.

The yields in the above-described syntheses of Compound 3 can be improved by suppressing side- or over-reactions that can occur as the product (Compound 3) comes in contact with its precursors. These side- or over-reactions can be suppressed by decreasing the residence time of the final process step (the step resulting in Compound 3). This reduction of residence time can be achieved by using a suitable flow operation rather than a batch operation at this step. The reactants are introduced in individual reactant streams which are combined and immediately mixed in a flow-through step. This can be achieved by combining the individual flow streams at a point near the inlet of a pump, and pumping the combined reactant stream through a static mixer, followed by immediate quench.

Alternatively, amide 3 may be reduced to the corresponding vinyl alcohol 4, and the alcohol is then reacted with nitro acid 6 to yield Compound 2.

Compound 2 is subsequently cyclized to yield Compound 1. The cyclization of 2 is conducted in a suitable solvent (e.g., hydrocarbons such as xylene, N-methylpyrrolidinone, Dimethylsulfoxide, diphenyl ether, Dimethylacetamide and the like as well mixtures of 2 or more thereof), at elevated temperature (e.g., between about 70 and about 190° C., preferably between about 80 and about 170° C., more preferably between about 100 and about 160° C., still more preferably between about 120 and about 150° C.), to produce a mixture of exo- and endo-isomers. This mixture is treated with a suitable base to complete the epimerization at the trans[5,6]-ring-junction (29) to the cis-isomer (30). The resulting mixture comprises the α- and β-isomers of each Compound 29 and 30, for a total of four isomers. The α-isomer of Compound 30 is a desirable intermediate in the synthesis of himbacine analogs, and is herein designated Compound 1.

The resulting mixture is dynamically resolved by treatment with a suitable base and preferential crystallization of the desired α-isomer using a suitable solvent. The equilibrium concentrations of the α- and β-isomers in solution are a function of the pH of the solution, which can be modified by addition a suitable base. Thus, the β-isomers can be converted to the desired α-isomers by addition of a suitable base. Simultaneously, in the presence of a suitable solvent, the α-isomer precipitates from the solution as a solid. In the dynamic resolution process, this precipitation tends to deplete the α-isomer from the solution, driving the equilibrium of the β to α conversion process from the β-isomer towards the α-isomer in the solution.

Suitable bases for the steps include, for example, triethylamine, 1,5-diazabicyclo[4,3,0]non-5-ene 1,4-diazabicyclo[2,2,2]octane, and 1,8-diazabicyclo[5,4,0]undec-7-ene, or mixtures of 2 or more thereof. Suitable solvent for crystallization includes hydrocarbon, alcohols, ethers, ketones, esters, xylene, N-methylpyrrolidinone. In some embodiments, the solvent is selected from ethanol, isopropyl alcohol, aryl alcohol alcohols, ethers, ketones, esters, xylene, N-methylpyrrolidinone, and the mixtures of 2 or more thereof. Advantageously, the exo-endo ratio for Compound 1 may exceed 90:10, and may also exceed 95:5. The α:β ratio at the nitro position may exceed 95:5, and for example may be 98.1:1.5.

mixture of alcohols to give crude Compound 8. To purify Compound 8, crude Compound 8 is isolated as its metal bisulfite salt 9 by treating with a metal bisulfite reagent selected from, $NaHSO_3$, $KHSO_3$, $Na_2S_2O_5$, and $K_2S_2O_5$. The bisulfite compound 9 is converted to the purified 8 by treating with a lower alkyl carbonyl compound (e.g., acetaldehyde, acetone, glyoxylic acid, or a salt of glyoxylate), and a carbonate base (e.g., $LIHCO_3$, $NaHCO_3$, $KHCO_3$, $Na_2CO_3$, $K_2CO_3$) in a biphasic system containing water and a water-immiscible solvent.

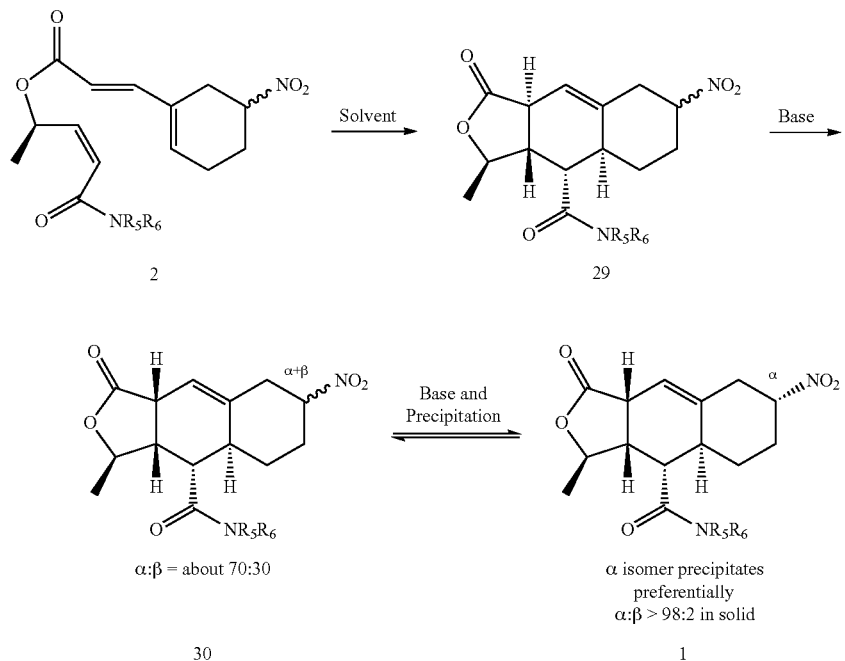

The carbon-carbon double bond and the nitro group of Compound 1 may then be reduced under suitable reduction conditions to yield amine 12. Suitable reduction conditions may include contact with a hydrogenation catalyst, such as one selected from standard noble metal catalysts (e.g., palladium on carbon, platinum on carbon, and rhodium on carbon, or a mixture thereof). The source of hydrogen can be hydrogen gas, formic acid, formates, and combinations thereof. Multiple catalysts may also be used. Amine 12 may then be converted to carbamate 13 by reaction with an alkyl haloformate (e.g., ethylchloroformate, ethylbromoformate, or ethyliodoformate). Carbamate 13 may then be converted to the carbamate acid 14 by reaction with a base such as, for example, a metal oxide or hydroxide, carbonate and bicarbonate, where the metal is selected from the group consisting of lithium, sodium, potassium, and magnesium, followed by reaction with a mineral acid. Sodium hydroxide is a preferred base. The acid 14 is subsequently converted to the corresponding aldehyde 15, which is reacted with phosphorus ester 16 to yield Compound 1.

Compound 6 may be prepared from acrolein and nitromethane following the scheme below. Nitromethane is treated with an inorganic base such as metal hydroxide (e.g., LiOH, KOH, NaOH, $Ca(OH)_2$), metal carbonate (e.g., $Li_2CO_3$, $Na_2CO_3$, $K_2CO_3$, $Cs_2CO_3$) and acrolein in a $C_1$ to $C_8$ alcohol (e.g., methanol, ethanol, propanol, isopropanol, butanol, sec-butanol, t-butanol, pentanols, and octanols) or a The compound 8 is cyclized by treating with a secondary amine (e.g., piperidine, pyrrolidine, piperazine, dialkylamines, and diarylalkylamines) and a carboxylic acid (e.g., aliphatic and aromatic carboxylic acids) in an organic solvent (e.g., $CH_2Cl_2$, chlorobenzene, t-butylmethylether, or toluene) to produce Compound 10.

There are two methods to convert Compound 10 to Compound 6, designated herein as Method C and Method D. In Method C, Compound 10 is first converted to Compound 6A by reacting 10 with a Wittig reagent. The $R_8$ in the Wittig reagent given in the scheme below is selected from $C_1$ to $C_{10}$ alkyl or arylalkyl groups. The Compound 6A is then converted to Compound 6 via an inorganic base- or acid-catalyzed hydrolysis. The applicable inorganic bases include, but are not limited to, alkaline hydroxide, carbonate, and phosphate bases. The applicable acids include, but are not limited to mineral and organic acids.

In method D, Compound 10 is converted directly to Compound 6 by reacting 10 with malonic acid in a suitable solvent or solvent mixture (e.g., hydrocarbon solvent including halogenated solvent, aromatic solvent and nitrogen-containing solvents). In some embodiments, the solvent is either pyridine or toluene, or a mixture thereof. Optionally, a catalyst (e.g., piperidine, pyrrolidine, piperazine, pyridine, and triethylamine) can be introduced to accelerate the reaction.

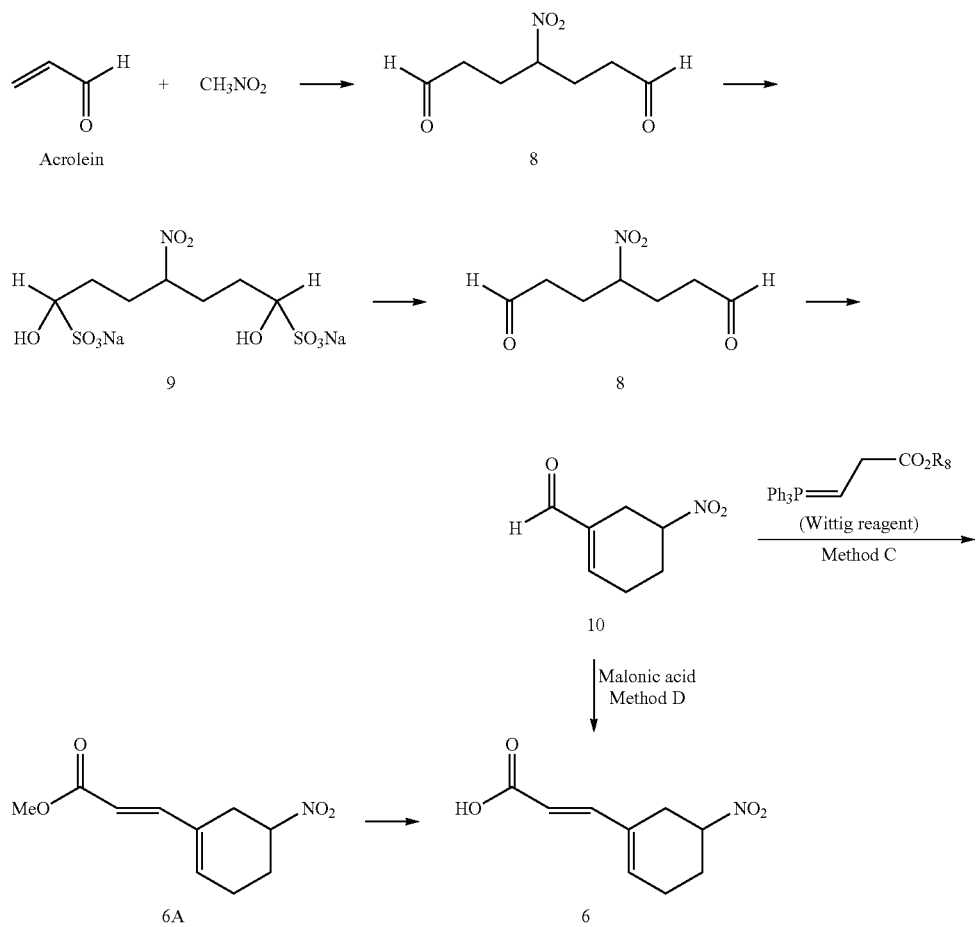

Compound 16 can be prepared following the scheme below starting from 5-bromo-2-methylpyridine N-oxide. The 5-bromo-2-methylpyridine N-oxide is first converted to Compound 35 by treating with an anhydride (e.g., aromatic acid anhydride, acetic anhydride, or trihalogenated acetic anhydride) in an applicable solvent (e.g., esters, $C_1$ to $C_{10}$ hydrocarbon solvent, or aromatic solvents, or a mixture thereof). Compound 35 is converted to Compound 36 by treatment with an alcohol (e.g., methanol, ethanol, propanol, isopropanol, butanols, and pentanols) at an elevated temperature of about 20 to about 80° C., preferably, about 30 to about 70° C., more preferably about 45 to about 55° C.

The synthesis of Compound 37 (with X being Cl) is disclosed in van den Heuvel, Marco et al, *J. Org. Chem.*, 69, 250-262 (2004). According to the present invention, Compound 36 is converted to Compound 37 according to the scheme below, by reacting with a leaving group reagent including a halogenating reagent (e.g., $SOCl_2$, $SOBr_2$, $PCl_3$, $PBr_3$, $PCl_5$, or $PBr_5$) or another proper leaving group reagent. In the scheme below, X is a leaving group selected from Halogens, esters, sulfonates, and phosphates.

Compound 37 is converted to Compound 38 by treating with a phosphite reagent. The phosphite reagent can be prepared from a dialkylphosphite or a diarylphosphite (e.g., $(R_9O)_2P(O)H$, wherein $R_9$ is selected from $C_1$-$C_{10}$ alkyl, aryl, heteroaryl, and arylalkyl groups) and a strong base (e.g., metal hydrides, $R_{10}Li$, and $((R_{10})_3Si)_2NLi$, wherein $R_{10}$ is selected from $C_1$ to $C_{10}$ alkyl and aryl groups).

Compound 38 is converted to Compound 16 by reacting with a fluoroaromatic borate reagent, $3\text{-}FC_6H_4B(OR_{11})_2$, wherein $R_{11}$ is selected from a group consisting of $C_1$ to $C_{10}$ alkyls, aryls, heteroaryls and hydrogen. The reaction is catalyzed using a palladium catalyst, $PdL_n$, wherein L is a ligand selected from $PR'_3$ wherein R' is selected from alkyl, aryl, alkylaryl, and $NR''_3$ wherein R'' is selected from alkyl, aryl, and alkylaryl. Alternately, palladium on carbon ("Pd/C") may be used as the catalyst. The preferred ligands are $PPh_3$, $P(o\text{-}Tol)_3$, and bipyridine.

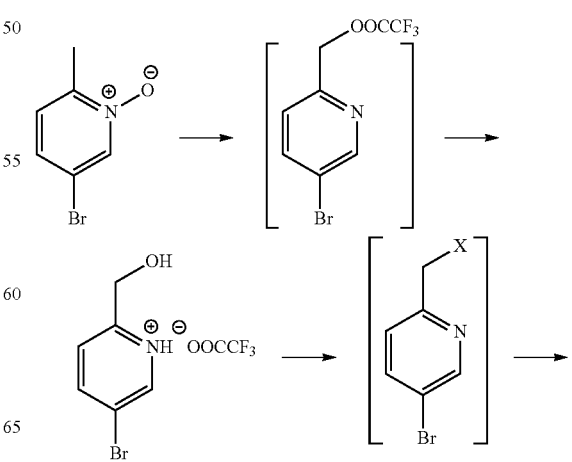

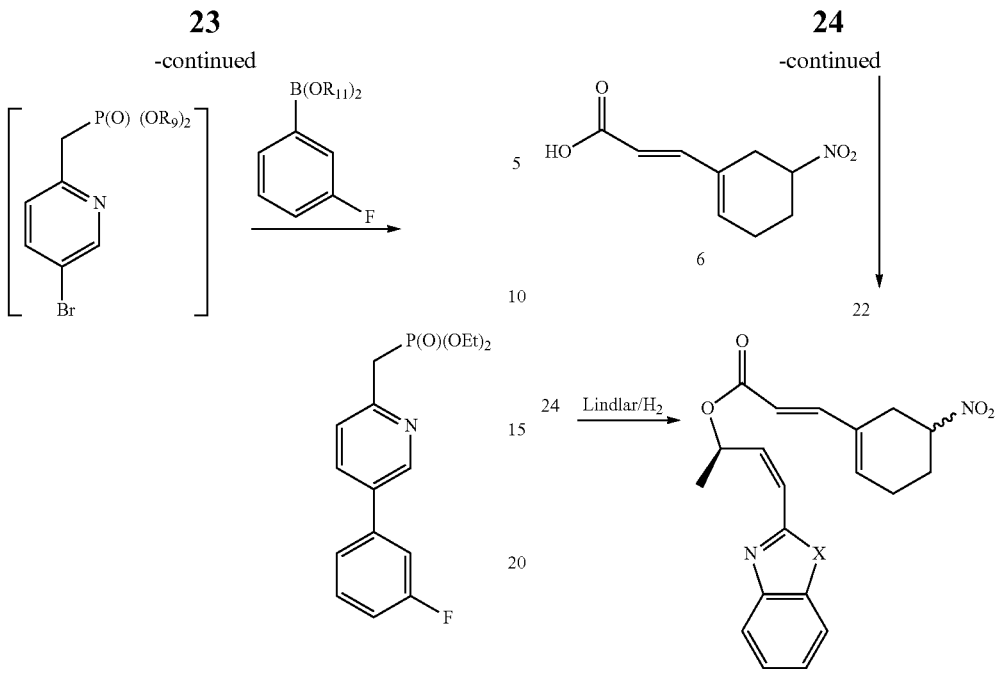
The following illustrates a general scheme for the synthesis of Compound 11 via the nitro-oxazole route:
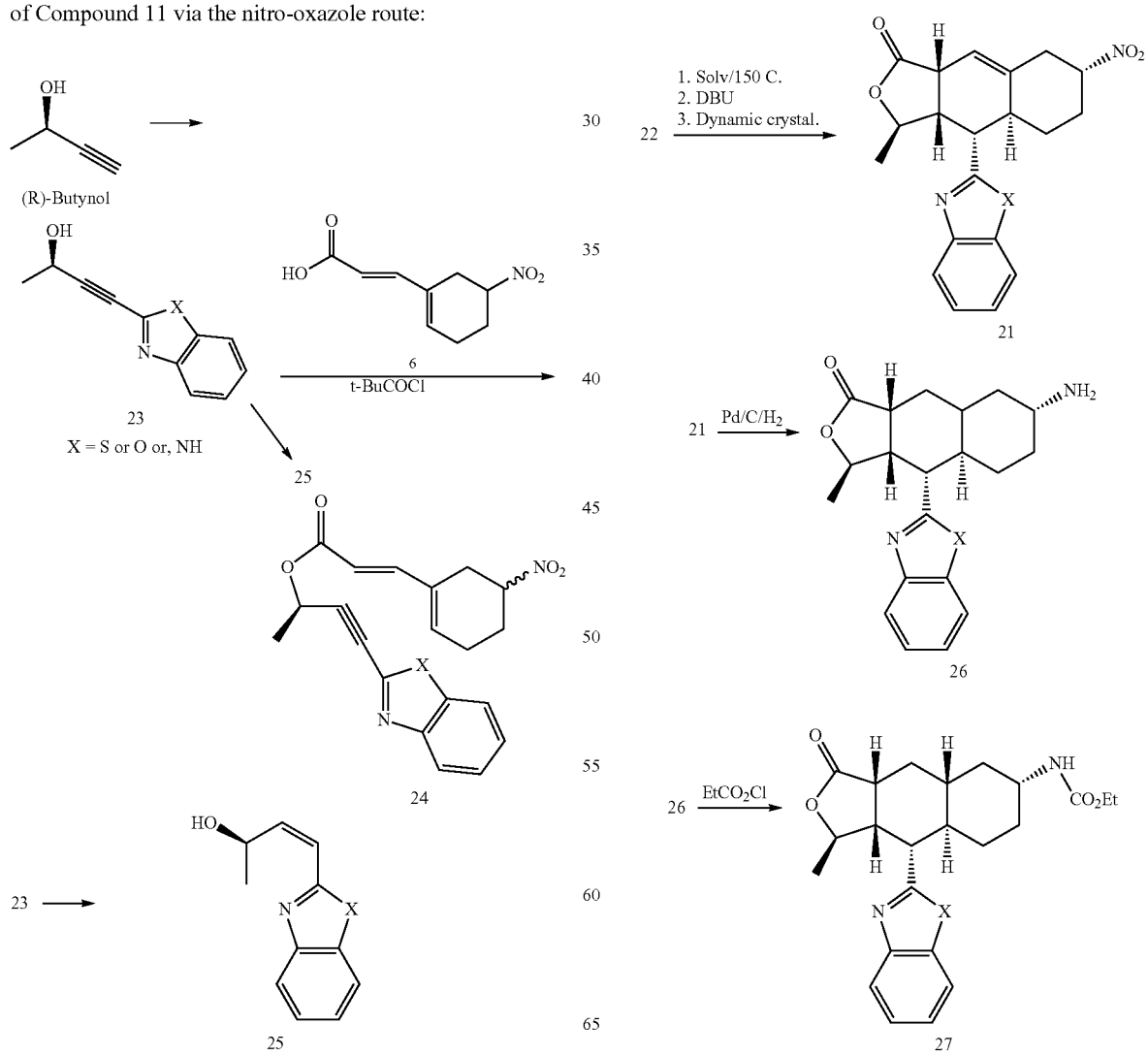

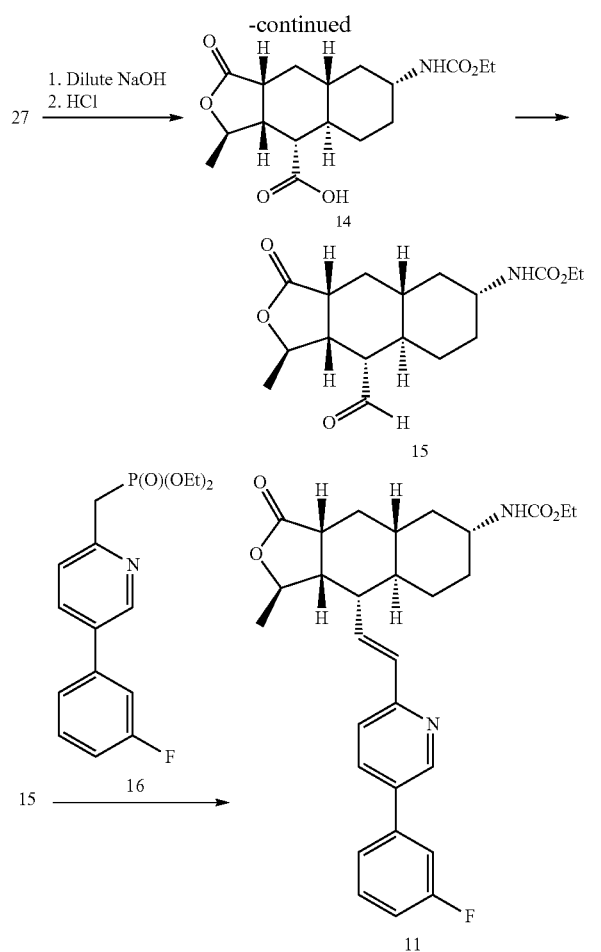

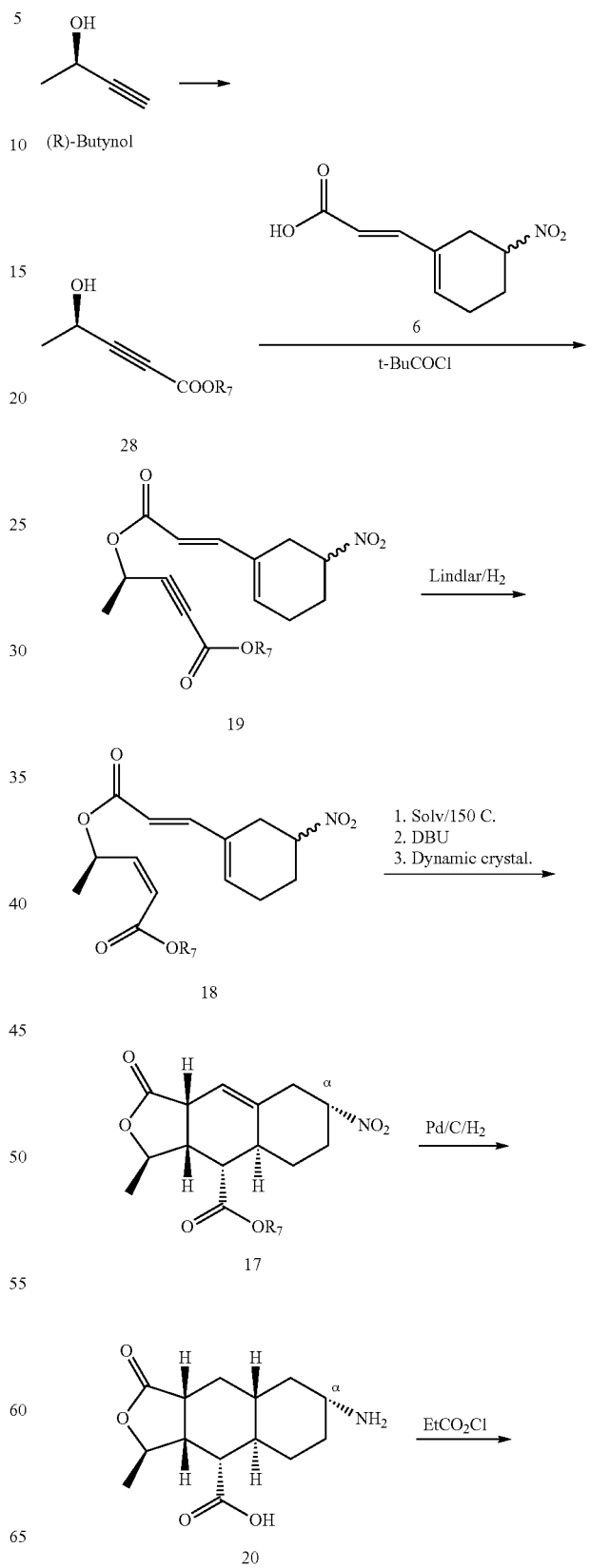

The following illustrates a general scheme for the synthesis of Compound 11 via the nitro-ester route:

(R)-butynol may advantageously be protected with, for example, THP. The THP-protected alcohol may then be permitted to react with a substituted benzothiazole, for example 2-chlorobenzothiazole, to yield Compound 23 (where X is S). The reaction may be conducted in a solvent, for example an organic solvent such as DMF, and in the presence of a base, for example triethylamine. Compound 23 may then be converted to Compound 22 by either of two routes: through vinyl alcohol 25, or through Compound 24. The latter route may be conducted by reacting Compound 23 with nitro acid 6 in the presence of an aromatic solvent such as, for example, toluene, to yield Compound 24. Compound 24 is subsequently reduced under hydrogenation conditions, for example in the presence of hydrogen and a Lindlar catalyst, to yield Compound 22. Compound 22 is then cyclized via a Diels-Alder reaction, followed by treatment with a base to yield Compound 21. The cyclization of 22 is conducted in a suitable solvent (e.g., hydrocarbons such as xylene, N methylpyrrolidinone, Dimethylsulfoxide, diphenyl ether, Dimethylacetamide and the like as well mixtures of 2 or more thereof), at elevated temperature (e.g., from about 70 to about 190° C., preferably from about 80 to about 170° C., more preferably from about 100 to about 160° C., still more preferably from about 120 to about 150° C.), to produce a mixture of exo- and endo-isomers. This mixture is treated with a suitable base to complete the epimerization to produce the cis-isomer (21). Suitable bases include, for example, triethylamine, 1,5-diazabicyclo[4,3,0]non-5-ene, 1,4-diazabicyclo[2,2,2]octane, and 1,8-diazabicyclo[5,4,0]undec-7-ene.

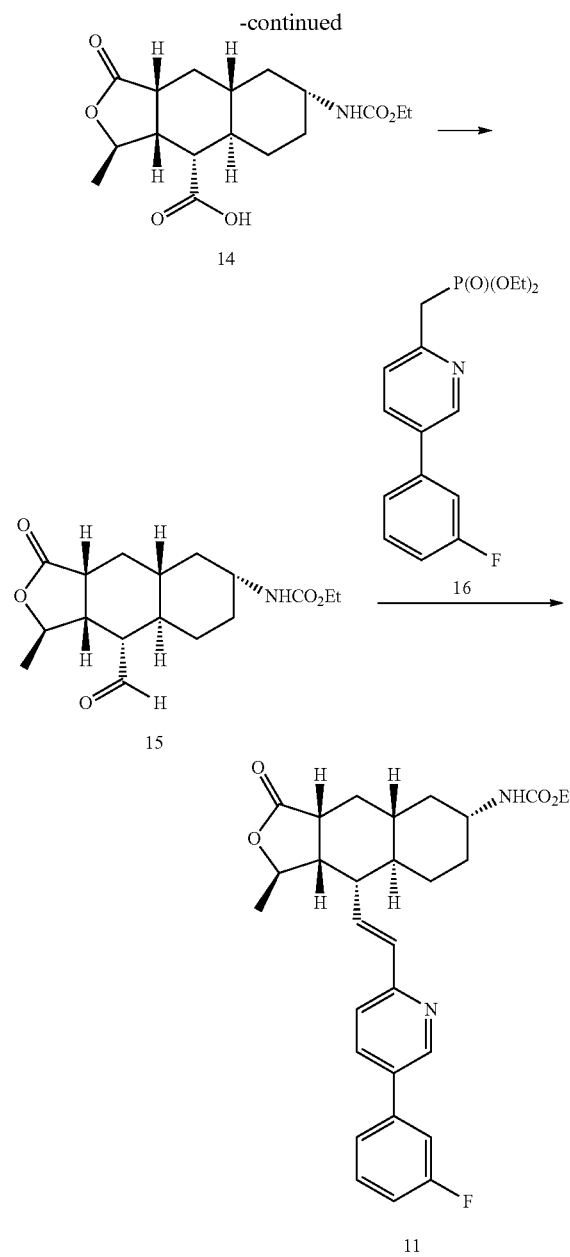

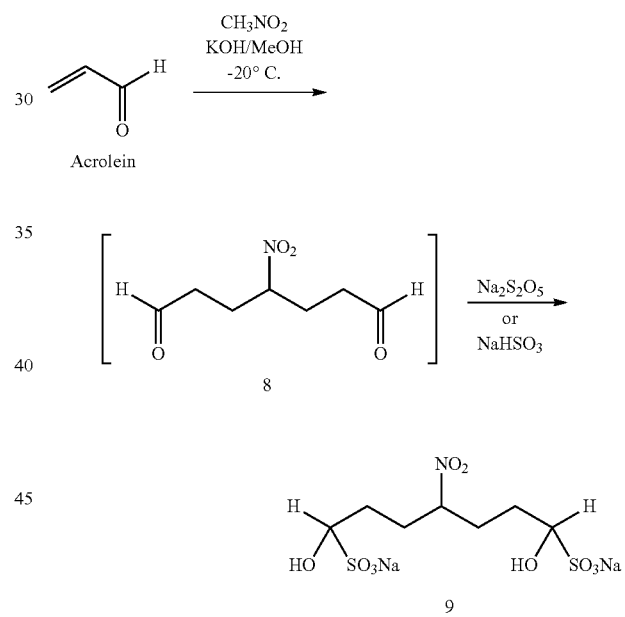

double bond and the nitro group of Compound 17 may then be reduced under suitable reduction conditions to yield amine 20. Suitable reduction conditions may include contact with a hydrogenation catalyst, such as one selected from standard noble metal catalysts. Multiple catalysts may also be used. A preferred reduction catalyst is palladium on carbon. The source of hydrogen can be hydrogen gas, formic acid, formates, and combinations thereof.

The experimental conditions disclosed herein are preferred conditions, and one of ordinary skill in the art can modify them as necessary to achieve the same products.

EXAMPLES

Example 1

Preparation of 3-(5-Nitro-cyclohex-1-enyl)-acrylic acid (Compound 6) and its Salt A. Preparation of Compound 9 from Acrolein (R)-butynol is converted to a benzyl ester 28 (where R₇ is benzyl). Compound 28 reacts with the mixed anhydride of the nitro acid 6 (prepared from 6 and pivaloyl chloride in the presence of a tert-amine base), in the presence of DMAP, to form Compound 19. Compound 19 is reduced under hydrogenation conditions, e.g., in the presence of hydrogen and a Lindlar catalyst, to yield ester 18. Ester 18 is subsequently cyclized to yield Compound 17 as follows. The cyclization of 18 is conducted in a suitable solvent (e.g., hydrocarbons such as xylene, N-methylpyrrolidinone, Dimethylsulfoxide, diphenyl ether, Dimethylacetamide and the like as well mixtures of 2 or more thereof), at elevated temperature (e.g., from about 70 to about 230° C., preferably, from about 80 to about 170° C., more preferably, from about 130 to about 160° C., still more preferably, from about 140 to about 150° C.), to produce a mixture of exo- and endo-isomers. This mixture is treated with a suitable base to complete the epimerization to the cis-isomer 17 as described previously. The carbon-carbon To a solution of potassium hydroxide (3.1 g, 0.05 mol) in methanol (450 ml) were added nitromethane (39 ml, 0.69 mol) and isopropanol (450 ml) under nitrogen atmosphere. The resulting mixture was cooled to a temperature between −20° C. and −25° C. Acrolein (120 ml, 1.74 mol) was then added slowly in about 3 to 3.5 hours while maintaining the temperature between −20° C. and −25° C. After stirring at the same temperature for 1 hour, the reaction was quenched with acetic acid (4 ml). The reaction mixture was warmed up to room temperature and a solution of sodium metasulfite (135 g, 0.67 mol) in water (700 ml) was slowly added at about 25° C. After stirring the resulting suspension for 1 hour, the mixture was cooled to 10° C. and stirred for another hour. White solid was obtained after filtration and drying under vacuum. The product was carried to the next step without further purification. Yield: 219 g, 83%. $^1$H NMR (400 MHz, DMSO-d$_6$) δ 1.41-1.64 (m, 2H), 1.76-1.99 (m, 6H), 3.79-3.85 (m, 2H), 4.63 (m, 1H), 5.44 (t, J=6.2 Hz, 2H).

B. Preparation of 4-Nitro-heptanedial

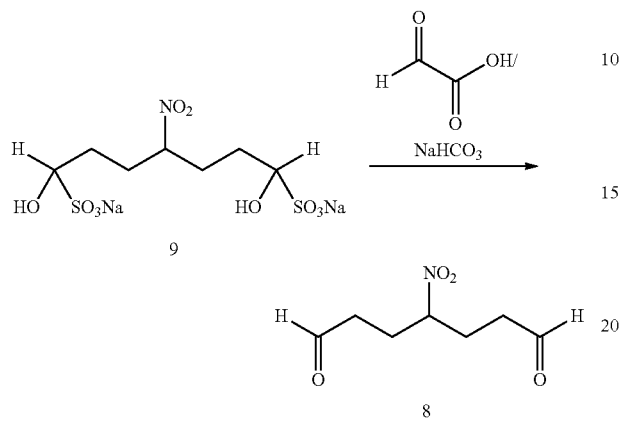

To a suspension of sodium 1,7-dihydroxy-4-nitro-heptane-1,7-disulfonate, 9, (219 g, 0.57 mol) in methylene chloride (1.6 L) was added a solution of glyoxylic acid (160 g, 1.7 mol) and sodium bicarbonate (150 g, 1.78 mol) in water (2 L). The resulting mixture was stirred at room temperature for 30 to 60 minutes until all solids were dissolved. The organic layer was split and the aqueous layer was extracted with methylene chloride twice (2×400 ml). Combined extracts were then concentrated to give a colorless oil. The product was carried to next step without further purification. Yield: 85 g, 86%. $^1$H NMR (400 MHz, CDCl$_3$) δ 2.09-2.24 (m, 4H), 2.58 (m, 4H), 4.61 (m, 1H), 9.77 (s, 2H). $^{13}$C NMR δ 26.2, 39.9, 86.9, 200.0.

C. Preparation of 5-Nitro-cyclohex-1-enecarbaldehyde

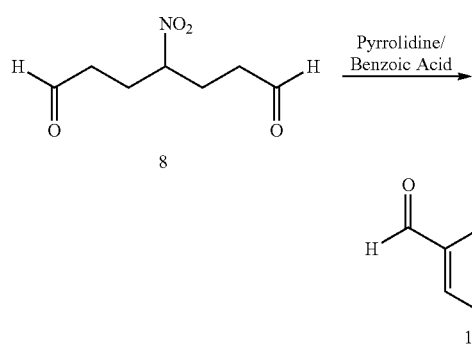

To a solution of 4-Nitro-heptanedial (35.2 g, 0.2 mol) in methylene chloride (0.7 L) were added pyrrolidine (2 ml, 0.024 mol) and benzoic acid (1.46 g, 0.012 mol), and the resulting mixture was refluxed for 10 to 15 hours. The reaction mixture was cooled to room temperature, washed with 1N HCl (170 ml), saturated with NaHCO$_3$ (170 ml) and water (170 ml) and concentrated to give brownish oil with a purity of about 80%. The product was carried to the next step without further purification. Yield: 32.2 g, 75%. $^1$H NMR (400 MHz, CDCl$_3$) d 2.29-2.34 (m, 2H), 2.46-2.64 (m, 2H), 2.85-2.88 (m, 2H), 4.74 (m, 1H), 6.86 (m, 1H), 9.50 (s, 1H).

D. Preparation of 3-(5-Nitro-cyclohex-1-enyl)-acrylic acid

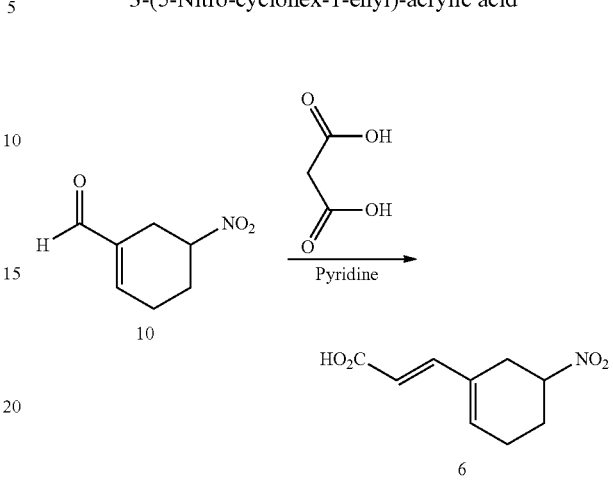

To a solution of 5-nitro-cyclohex-1-enecarbaldehyde (18 g, 0.116 mol) in pyridine (36 ml) was added masonic acid (41 g, 0.394 mol). The resulting suspension was heated to 60° C. for about 7 hours. After cooling to a temperature between 15° C. and 20° C., 6N HCl (72 ml) was slowly added into the reaction mixture to adjust the pH to between 1.5 and 2 while maintaining the temperature between 20° C. and 25° C. The mixture was then extracted with methylene chloride three times (1×180 ml, 2×90 ml). The combined extracts were washed with 1N HCl (48 ml), water (48 ml) and concentrated to a volume of 36 ml. The concentrate suspension was cooled to 0° C. and 5° C. for 1 hour. Light yellow solid was obtained after filtration and drying under vacuum. Yield: 10 g, 60%. Mp 158-160° C. $^1$HNMR (400 MHz, DMSO-d$_6$): δ 2.10-2.33 (m, 4H), 2.73 (m, 2H), 4.96 (m, 1H), 5.83 (d, J=20 Hz, 1H), 6.28 (s, 1H), 7.27 (d, J=20 Hz, 1H), 12.3 (s, 1H).

Example 2

Alternative Method for Preparing 3-(5-Nitro-cyclohex-1-enyl)-acrylic acid (Compound 5) via Wittig Reagent

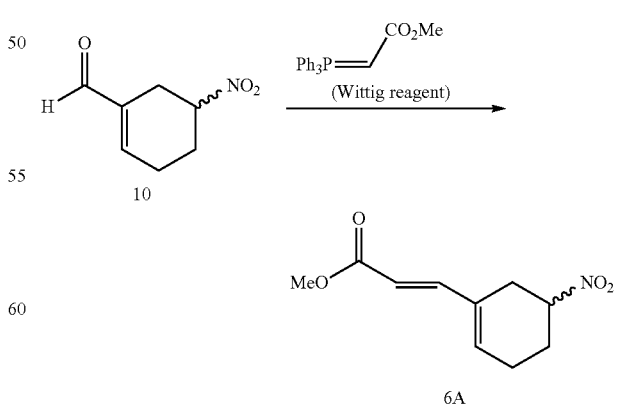

To a solution of 10 (67 g, 432 mmol) in 1 L of methanol at 0° C. was added 144.4 g (432 mmol) of the Wittig reagent.

The resulting mixture was agitated at 0° C. for 3 hrs. The solvent was removed under reduced pressure. The residue was extracted with MeOBu-t twice. The extract was filtered to remove any solid, washed with brine, and concentrated. The residue was chromatographed on a silica gel column, eluting with hexane/ethyl acetate (10/1) to give 9.2 g cis and 55.1 g (60.4%) trans product. $^1$H NMR (CDCl$_3$) d 7.31 (d, J=11.3 Hz, 1H), 6.18 (m, 1H), 5.84 (d, J=15.9 Hz, 1H), 4.74-4.68 (m, 1H), 3.76 (s, 3H), 2.81-2.74 (m, 2H), 2.50-2.04 (m, 4H).

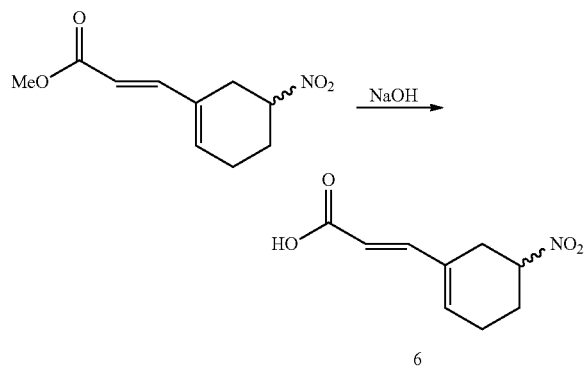

Next, to a flask were added 2.1 g of the methyl ester, 9.6 ml of MeOH and 2.4 ml of water. To the mixture at about 5° C. was added dropwise 0.96 ml of 50% NaOH. The mixture was allowed to warm to room temperature and stirred at this temperature for about 24 hrs. The reaction mixture was neutralized with HOAc to pH between 4 and 5 and the methanol was removed under reduced pressure. The residue was extracted with 3×50 ml EtOAc. The EtOAc layer was concentrated to give 1.5 g of nitroacid 6 (76.5%).

Example 3

Preparation of Compound 3a

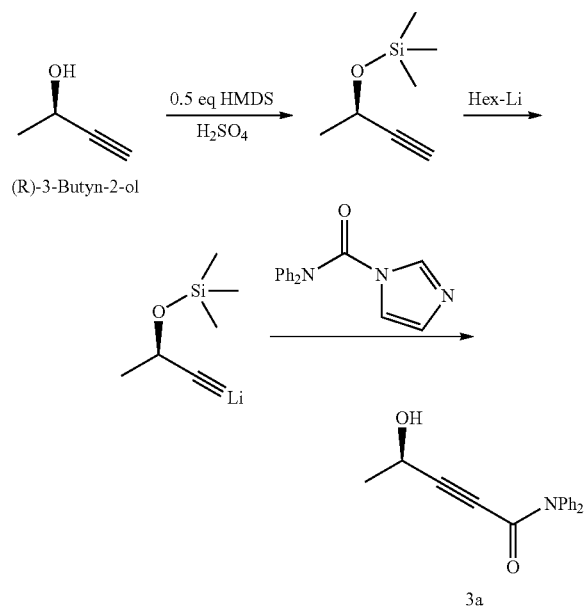

The following procedures can be operated on either the racemic or the enantiopure starting butyn-2-ol. To a stirred solution of sulfuric acid (conc., 40 μL) in THF (240 mL) were sequentially added (R)-3 butyn-2-ol (40 g, 0.57 mol) and then hexylmethyldisilazane (49.6 g, 0.31 mol) at room temperature. The solution was refluxed for 3-4 hours and then slowly cooled to −40° C. The resulting mixture was slowly charged in hexyllithium (2.5M in hexane, 249 mL, 0.62 mol) while maintaining the temperature at −40° C. This solution and a solution of diphenylcarbamylimidazole (180 g, 0.68 mol) in a mixed solvent of THF (1088 mL) and toluene (435 mL) were mixed using pumps through a chilled static mixer and directly quenched into 5N sulfuric acid (560 mL, −5° C.). The quenched solution was warmed to 25° C. and stirred for 1 hour. The organic layer was separated, washed with 5N sulfuric acid (80 mL) and then twice with 10% brine (200 mL each time). The pH of the final brine wash was adjusted to 5-7 with a 5% NaHCO$_3$ solution. The organic layer was then distilled and replaced with toluene (440 mL). The toluene solution was added to heptane (400 mL) at 85° C., cooled slowly to 20° C. and filtered. The filtered cake was washed with a mixed solution of toluene (80 mL) and heptane (80 mL). The cake was then dried in vacuum oven at 50° C. to afford the title compound in 84% molar yield (120.6 g, purity 99%). Mp 105° C. $^1$H NMR (400 MHz, DMSO-d$_6$) δ 1.04 (d, J=6.4 Hz, 3H), δ 4.27 (dq, J=5.6 Hz, 6.4 Hz, 1H), δ 5.49 (d, J=5.6 Hz, 1H), δ 7.2-7.5 (m, 10H); $^{13}$C NMR (DMSO-d6) δ 23.7, 56.3, 76.9, 96.4, 126.8, 127.0, 128.5, 129.2, 129.4, 129.6, 141.5, 142.2, 152.9.

Example 4

Preparation of Compound 7a

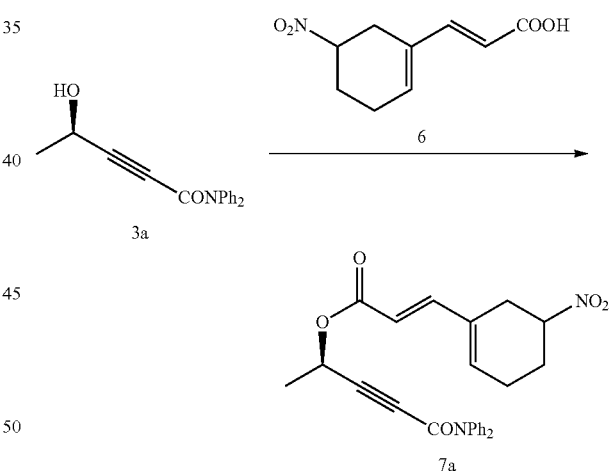

To a flask were charged sequentially Compound 6 (90 g, 0.46 mole) and toluene (500 mL). The suspension was cooled to about 0° C., and N-methylmorpholine (91 mL, 0.83 mole) and trimethylacetyl chloride (56 mL, 0.46 mole) were slowly added while keeping the reaction temperature below 5° C. The reaction mixture was agitated for 1 hour at 0° C. and assayed for completion of formation of mixed anhydride (<10% of UB remains). A solution of 3a (100 g, 0.38 mole) in toluene (400 mL) and THF (220 mL) was added while keeping the reaction temperature below 5° C. This was followed by addition of a solution of 4-dimethylaminopyridine (5.5 g, 0.046 mole) in THF (45 mL). The mixture was agitated at about 0° C. for 8-12 hours until reaction completion (<0.2% EB remains). Reaction was quenched by adding a solution of 2.0 N H$_2$SO$_4$ (400 mL), warmed up to 25° C. and filtered through a pad of celite. The layers were separated and the organic layer was washed with 5% K$_2$CO$_3$ solution (3×300 mL) to remove excess 6 (<1% of 6 remains). The mixture was washed with 5% NaCl. solution (300 mL), filtered through a pad of celite, and concentrated to about 500 mL final volume. Solution yield 90-95%. $^1$H NMR (CDCl$_3$, 400 MHz) δ 7.05-7.35 (m, 11H), 6.13 (br, 1H), 5.62 (dd, J=16, 4 Hz, 1H), 5.31 (q, J=7 Hz, 1H), 4.67 (m, 1H), 2.62-2.78 (m, 2H), 2.58 (br, 2H), 2.05 (m, 2H), 1.22 (d, J=7 Hz, 3H).

Example 5

Preparation of Compound 2a

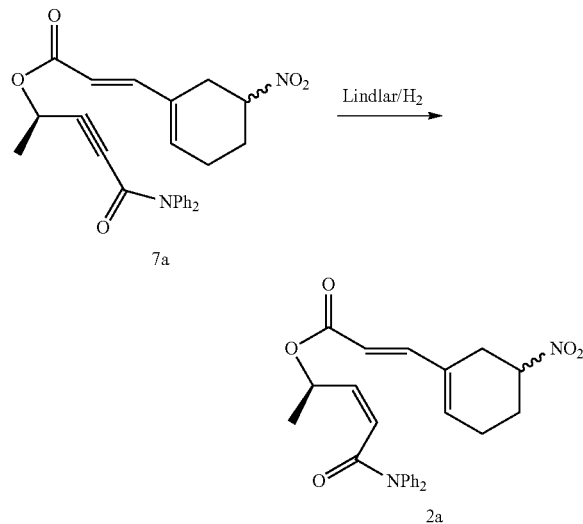

To a solution of 7a in toluene (200 mL, 50.0 g active, 112.5 mmol) were charged Lindlar catalyst (2.5 g of 5% Pd/CaCO$_3$ with 5% Pb poisoned, 1.2 mmol) and quinoline (1.5 mL, 11.6 mmol). The mixture was hydrogenated using 100 psi hydrogen at 25-30° C. until reaction completion as judged by HPLC. After removal of catalyst by filtration, toluene was replaced with ethyl alcohol by regulated vacuum distillation of about 40° C. The product was dynamically crystallized from ethyl alcohol (180 mL) at 40° C. in the presence of triethyl amine (8.5 mL). The reaction mixture was slowly cooled to 5° C. over a period of 4 hours. After stirring at 5° C. for 3 hours, the product was filtered and washed with cold ethyl alcohol. The product was dried at 60° C. in a vacuum oven with nitrogen purge overnight to give 2a as a yellow crystalline solid. Yield: 73.7%. Mp 113-115° C. $^1$H NMR (400 MHz, CDCl$_3$) δ 1.48 (d, J=6.4 Hz, 3H), 2.21-2.46 (m, 4H), 2.80 (m, 2H), 4.71 (m, 1H), 5.81-5.91 (m, 3H), 6.19 (m, 1H), 6.29 (q, J=6.4 Hz, 1H), 7.28-7.37 (m, 11H).

Example 6

Preparation of Compound 1a

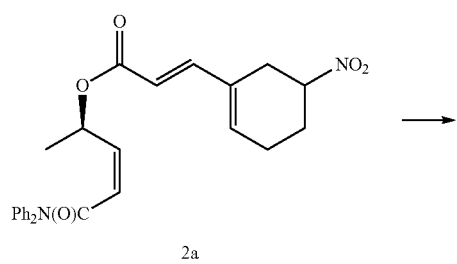

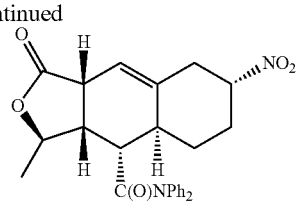

1a

Into a 2 L 3-neck round bottom flask was placed 2a (25 g, 0.056 mol) and ethyl acetate (210 mL). The contents were stirred until Compound 2a completely dissolved. The solution was washed with 0.25 M H$_2$SO$_4$ (75 mL) and with water (3×75 mL). The organic phase was concentrated under reduced pressure to about 200 mL, and 1-methyl-2-pyrrolidinone (50 mL) was added. The solution was heated under distillation mode until a temperature of 145° C. was attained. The solution was held at this temperature for 3.5 h. The solution was cooled to room temperature, and DBU (0.57 mL, 6.8 mol %) was added. The solution was stirred for 1 h and was quenched with 0.1 M H$_2$SO$_4$ (125 mL) and the product was extracted into ethyl acetate (125 mL). The organic phase was washed with water (125 mL) and was treated with DARCO-G60 (2.5 g) at 65° C. for 1 h. The suspension was filtered through a pad of Celite while the solution remained hot. The solution was concentrated by atmospheric distillation to 38 mL. The remaining ethyl acetate was replaced with isopropyl alcohol by azeotropic distillation. The volume of the solution was adjusted to 225 mL. The solution was diluted with ethyl alcohol (denatured with 0.5% toluene, 100 mL). The solution was slowly cooled to about 65° C., and DBU (0.29 mL, 3.4 mol %) was added. The suspension was slowly cooled to 15° C. and held at this temperature for 5 h. The product was filtered and washed with a 2:1 mixture of isopropyl alcohol and ethyl alcohol (50 mL). 19.3 g was obtained upon drying for 24 h at 50° C. (90.2 wt % purity, 17.4 g active, 72.5% yield). Mp 151.8° C. $^1$H NMR (400 MHz, CDCl$_3$): δ 0.99 (m, 1H), 1.56 (d, J=6.0 Hz, 3H), 2.03 (m, 1H), 2.25-2.31 (m, 1H), 2.42-2.53 (m, 2H), 2.62-2.76 (m, 3H), 2.86-2.91 (m, 1H), 2.96-3.00 (m, 1H), 4.28-4.36 (m, 1H), 4.67-474 (m, 1H), 5.42 (br s, 1H), 7.22-7.53 (m, 10H).

Example 7

Preparation of Compound 13a

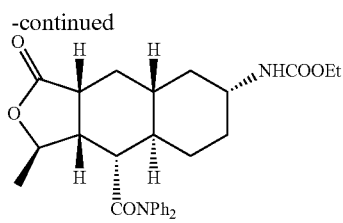

13a

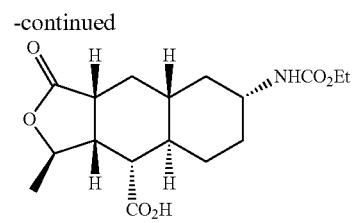

14a

To a three-neck flask equipped with an agitator, thermometer and nitrogen inlet were sequentially added 1a (100 g), THF (600 ml), 10% palladium on carbon (50% wet, 35 g) and water (400 ml). The mixture was agitated for about 10 minutes at room temperature and then heated to about 50° C. Formic acid (70 ml) was added slowly while the temperature was maintained between 45 and 55° C. The reaction mixture was agitated for 4 hours at 45-55° C. After the reaction was judged complete by HPLC, the reaction mixture was cooled to 20° C. and the pH was adjusted to 1-2 with 25% $H_2SO_4$ (60 mL). THF (200 mL) was added to the reaction mixture, which was then filtered through a pad of Celite to remove the catalyst. A mixed solution of THF (300 mL), water (300 ml) and 25% $H_2SO_4$ (5 mL) was used to rinse the flask and catalyst, and filtered through the Celite. The combined solution containing compound 12a was charged back into a clean flask and the mixture was cooled to below 10° C. The pH was adjusted to about 9 with 25% NaOH (30 mL) at below 10° C. and NaCl (150 g) was then added. The mixture was warmed to 20° C. and two phases were separated. The aqueous phase was extracted with THF (400 mL) and the combined organic phases were washed with a brine solution (40 g of NaCl in 200 mL of water). The organic layer was cooled to 5° C. and triethyl amine (56 mL) was added. Then ethyl chloroformate (23.6 mLml) was added slowly. The mixture was warmed to 20° C. and stirred for 30 minutes. After the reaction was judged complete, 200 ml of MTBE and 100 mL of water were added to the reaction mixture, followed by the slow addition of 100 mL of 25% $H_2SO_4$. The two phases were separated and the organic layer was washed with 200 ml of 12% $H_2SO_4$. The organic layer was then concentrated and azeotropically distilled with 2B ethanol and 250 ml water was added at 70-80° C. The compound 13a was precipitated out from ethanol-water with seeding at 55-65° C. After agitating for 1 hour at 55-65° C., 150 ml water was added at this temperature and held for 1 hour. After cooling to 15-25° C., the mixture was agitated for an additional 3 hours at 15-25° C. and then the product was filtered and washed with ethanol-water. The product was dried at 50-60° C. to provide an off-white solid (86 g, Yield: 85%). Mp 188.2° C. $^1$HNMR (CDCl$_3$) δ 7.25-7.55 (m, 10H), 4.89 (m, 1H), 4.51 (bs, 1H), 4.09 (d, J=6.98 Hz, 2H), 3.49 (brs, 1H), 2.41 (m, 2H), 2.25 (m, 1H), 2.06 (d, J=10.8 Hz, 2H), 1.96 (d, J=10.9 Hz, 1H), 1.83 (ddd, J=13.5, 6.09, 2.51 Hz, 1H), 1.63 (m, 1H), 1.52 (d, J=5.8 Hz, 3H), 1.23 (m, 5H), 1.17 (q, J=11.5 Hz, 2H), 0.92 (q, J=11.5 Hz, 1H). MS (ESI) for M+H calcd. 491 Found: 491.

Example 8

Preparation of Compound 14a

To a 250-mL 3-neck flask equipped with an agitator, thermometer, and a reflux condenser, were added 10 g of 13a (20.4 mmol) and THF (50 mL). To this solution was added an aqueous solution of 5% (w/w) sodium hydroxide (50 mL). The reaction mixture was then heated to and agitated at 40° C. for about 4 hours. When the hydrolysis reaction was judged complete, toluene (50 mL) was added and the mixture was agitated at a rather fast rate for about 10 minutes. The organic phase containing the by-product was separated from the aqueous phase containing product. The organic phase was back-extracted with 5% aqueous NaOH solution (50 mL). The combined aqueous solutions were extracted twice with toluene (2×50 mL) and the organic extracts were discarded. To the aqueous solution were added a solvent mixture of toluene (25 mL) and THF (50 mL). The resulting mixture was cooled to between 0 to 5° C. A 2 N hydrochloric acid aqueous solution (about 59 mL) was added to adjust the pH of the mixture from ~13 to 2.5 at 0 to 5° C. The aqueous phase was then separated from the organic phase and extracted with a solvent mixture of toluene (25 mL) and THF (50 mL). The organic phase and organic wash were combined and diluted with THF (50 mL). The mixture was then concentrated atmospherically to a final moisture content of ≦0.05% by repeated distillations, if necessary. The crude product was used in the next step without further isolation and purification (containing 6.80 g, 99% yield). $^1$H-NMR (CD$_3$CN) δ 9.72 (bs, 1H), 7.17-7.41 (Ph in toluene), 5.45 (bs, 1H), 4.68 (dt, J=5.90, 16.0, 1H), 4.03 (q, J=7.10, 2H), 3.45-3.50 (m, 1H), 2.50-2.65 (m, 2H), 2.45 (dd, J=5.64, 11.5, 1H), 2.36 (methyl in toluene), 1.83 (m, 4 protons), 1.34-1.50 (qt, J=2.91, 11.0, 1H), 1.32 (d, J=5.91, 3H), 1.15-1.25 (m, 6H), 0.95-1.05 (m, 2H).

Example 9

Preparation of Compound 36

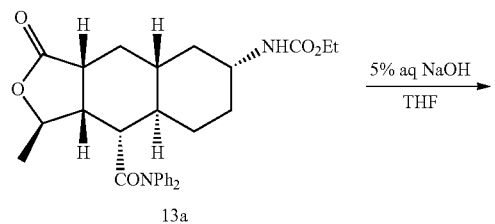

13a

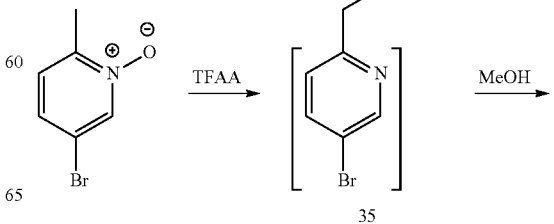

35

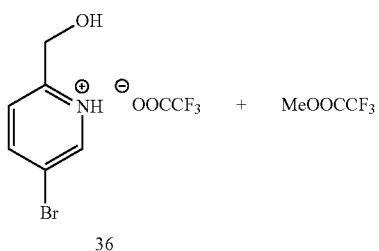

To a solution of 5-bromo-2-methylpyridine N-oxide (10.0 g, 5.32 mmol) in EtOAc (50.0 ml) at 0° C. was added dropwise trifluoroacetic anhydride (9.8 ml, 6.92 mmol.) while keeping the temperature below 50° C. After the completion of the addition, the mixture was heated to between 75 and 80° C. and stirred for at least 1 h. HPLC assay of the mixture indicated reaction completion when 5-bromo-2-methylpyridine N-oxide is <5%.

Upon completion, the mixture was cooled below 50° C. and MeOH (10.0 ml) was added. The mixture was heated for at least 1 h at 50° C. The solution was concentrated under vacuum and MeOH was removed by displacement with EtOAc (40.0 ml) and concentrated to a volume of 30 ml. To the concentrate was added toluene (20.0 ml) and the solution cooled to −10° C. over 2 h. The crystalline solid was filtered and washed with cold toluene and dried overnight under vacuum at 35° C. to provide 10.1 g (63%) of 36. Mp 89-92° C. $^1$H NMR (DMSO-d$_6$) δ 4.56 (s, 2H), 7.49 (d, 1H), 8.1 (dd, J=2.3, 2.3 Hz, 1H), 8.64 (d, J=2.1 Hz, 1H).

Example 10

Preparation of Compound 16

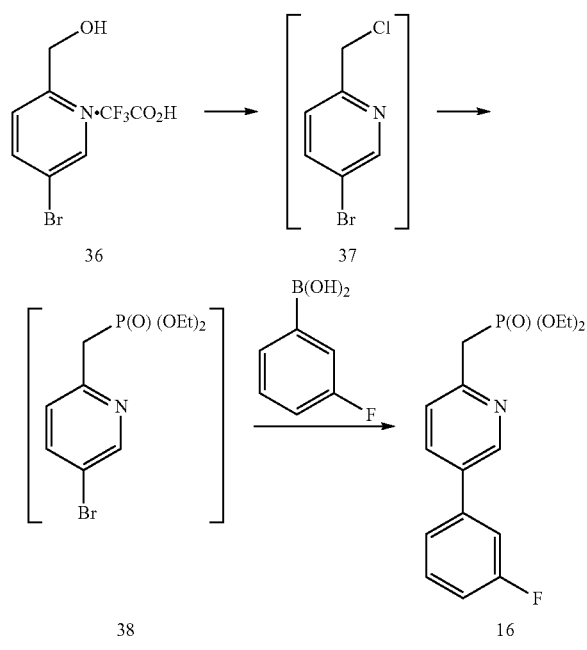

A. Preparation of 37

A slurry of 36 (10.0 g, 33.1 mmol) in TBME (100 ml) was treated with 20% potassium carbonate (20 ml) solution and stirred at room temperature for 1 h. The layers were separated and the organic layer was washed with water. The TBME and water were removed by atmospheric distillation and azeotropic distillation with acetonitrile (100 ml) and further concentrated under vacuum to a volume of 40 ml. A Karl Fischer was performed to confirm the removal of water (KF≦0.2). To the acetonitrile concentrate was added dropwise thionyl chloride (3.2 ml, 43.7 mmol) while keeping the temperature below 45° C. The reaction mixture was then heated at 45° C. for 2 h at which time an HPLC assay indicated complete reaction. The reaction mixture was cooled to 25° C. and quenched with water (20 ml) while keeping the temperature below 40° C. The reaction mixture was slowly poured into a mixture of 20% sodium carbonate (40 ml) and toluene (100 ml), stirred for 10 min and the layers were partitioned. The toluene extract was concentrated under reduced pressure to a volume of about 20 ml. A KF was performed to confirm the removal of water (KF≦0.2).

B. Preparation of 38

To a dry reaction vessel was charged a solution of lithium bis(trimethylsilyl) amide 1.3M in THF (51 ml, 66.2 mmol) and diethyl phosphite (13 ml, 101.6 mmol) while keeping the temperature under 25° C. The solution was stirred at 25° C. for at least 1 h. The toluene solution containing 37 from above was added over 1 h and the resulting mixture was stirred at 25° C. for at least 2 h at which time an HPLC assay indicated complete reaction. Upon completion, the solution was quenched into 5% sodium chloride (50 ml). The aqueous layer was extracted with toluene (50 ml). The combined organic layer was concentrated under reduced pressure to a volume of about 20 ml. Toluene (80 ml) was then added and the solution was washed with a 20% solution of potassium carbonate to remove diethyl phosphate, confirmed by $^1$H NMR (<20 mol %). The toluene solution was then washed with water and concentrated under reduced pressure to a volume of about 40 ml of Compound 38 solution.

C. Preparation of 16

To a reaction vessel was charged sodium carbonate (8 g; 75.5 mmol), 30 ml of water and stirred until dissolved. To this solution were added 3-fluorophenylboronic acid (6 g; 42.9 mmol) and 5% Pd/C 50% wet (0.5 g). The toluene solution of Compound 38 from above was then added and the mixture was heated to 75° C. for at least 5 h at which time an HPLC assay indicated complete reaction. Upon completion, the reaction mixture was cooled to 25° C. and filtered to remove the Pd/C catalyst. The layers were separated and the organic layer was washed and concentrated under reduced pressure to about 20 ml. Heptane (20 ml) was slowly added, seed crystals were added, and the mixture was cooled to −10° C. over 2 h. The crystalline solid was filtered, washed with heptane and dried overnight under vacuum at 30° C. to provide 8 g (75%). Mp 61-63° C. δ 1.3 (t, J=7.08 Hz, 3H), 3.42 (s, 1H), 3.49 (s, 1H), 4.1 (q, J=7.08 Hz, 2H), 7.04-7.11 (m, 1H), 7.23-7.3 (m, 1H), 7.32-7.3 (m, 1H), 7.32-7.36 (m, 1H), 7.39-7.48 (m, 1H), 7.81 (ddd, J=8.08, 2.3, 0.41 Hz, 1H), 8.74 (d, J=2.36, 1H).

Example 11

Preparation of Compound 23a

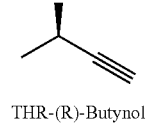
THR-(R)-Butynol

+ 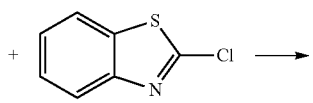

→

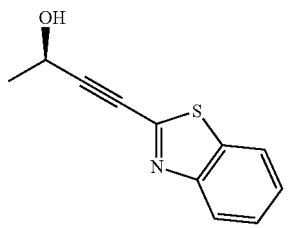
23a

To a flask were added 21 g (124 mmol) of 2-chlorobenzothiazole chloride, 30 g of KI, 150 ml of DMF, 2.7 g of CuI, 8.4 g of Pd(PPh$_3$)$_4$, 50 ml of Et$_3$N, and 118 ml of THP protected (R)-butynol. The mixture was stirred at room temperature for 18 hrs. Most of the solvent was removed under reduced pressure. Water was added and the product was extracted with a mixture of t-BuOMe and hexane. The organic layer was washed with brine and concentrated to give an oil. The oil was dissolved in 250 ml of MeOH and treated with TsOH for the deprotection. The mixture was heated at 50° C. for a few hrs. The pH was adjusted to between 7 and 8 with NaOH. Most of the solvent was removed. The residue was chromatographed on a silica gel column, eluting with EtOAc/hexane to give 19.7 g of 23a (78%). $^1$H NMR (CDCl$_3$) δ 7.98-7.96 (m, 1H), 7.76-7.74 (M, 1H), 7.45-7.33 (m, 1H), 4.82-4.76 (m, 1H), 3.43 (d, J=5.4 Hz, 1H), 1.55 (d, J=6.7 Hz, 3H).

Example 12

Preparation of Compound 24a

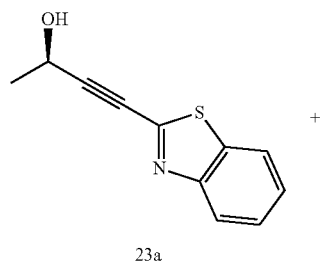
23a

+

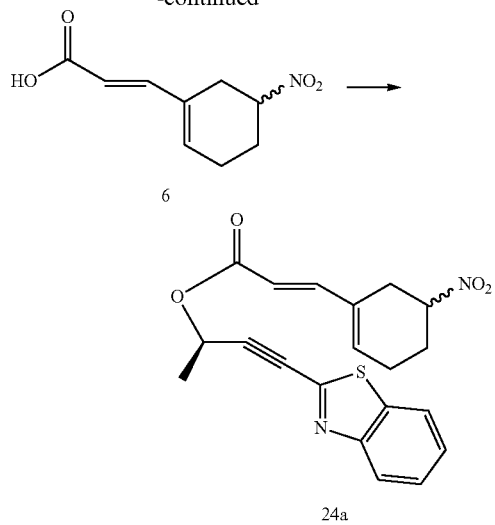
6

→

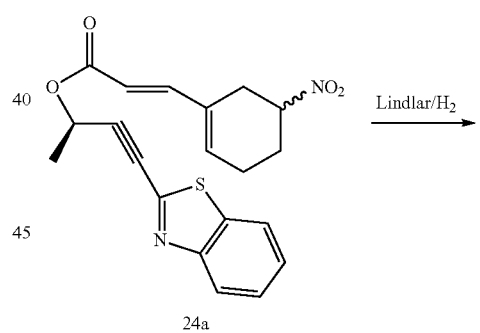
24a

The same procedure for the preparation of In described above in Example 4 was followed starting with 15 g of 23a to give, after column purification, 17 g of 24a. $^1$H NMR (CDCl$_3$) δ 7.99-7.97 (m, 1H), 7.79-7.77 (m, 1H), 7.48-7.35 (m, 2H), 7.31 (d, J=15.9 Hz, 1H), 6.15 (bs, 1H), 5.80-5.74 (m, 2H), 4.72-4.58 (m, 1H), 2.82-2.65 (m, 2H), 2.50-2.05 (m, 4H), 1.61 (d, J=6.7 Hz, 3H).

Example 13

Preparation of Compound 22a

24a

Lindlar/H$_2$ →

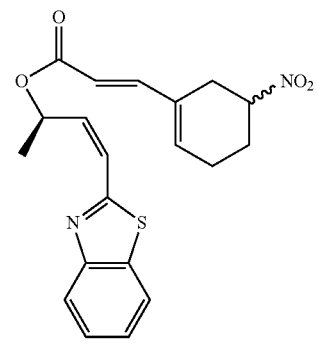
22a

The same procedure for the conversion of 7 to 2 (Example 5) was followed starting from 15 g of 24a to give, after column purification, 17 g product. $^1$H NMR (CDCl$_3$) δ 8.18 (d, J=8.4

Hz, 1H), 7.98 (d, J=8.4 Hz, 1H), 7.45-7.37 (m, 1H), 7.32-7.28 (m, 1H), 7.24 (d, 15.8 Hz, 1H), 6.59 (dd, J=11.8, 1.3 Hz, 1H), 6.55-6.40 (m, 1H), 6.15-6.08 (m, 1H), 6.00 (dd, J=11.8, 8.2 Hz, 1H), 5.76 (d, J=15.8 Hz, 1H), (m, 1H), 2.80-2.65 (m, 2H), 2.46-2.05 (m, 4H), 1.50 (m, 3H).

Example 14

Preparation of Compound 21a via Diels-Alder Reaction

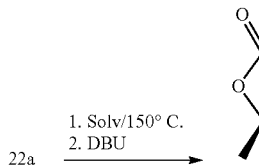
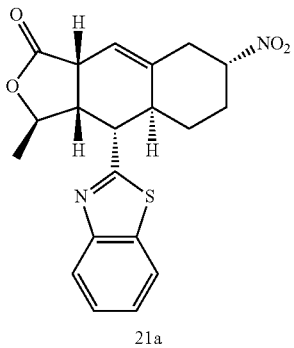

The same procedure for the conversion of 2a to 1a (Example 6) was followed starting from 0.34 g of 22a. The ratio of exo:endo was determined by HPLC and NMR and found to be 60:40.

Example 15

Preparation of Compound 19a

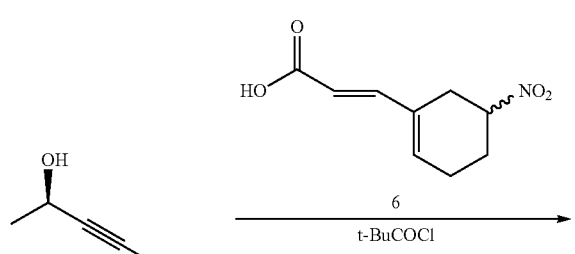

To a flask under nitrogen were added 1.48 g of nitro acid 6 and 9 ml of toluene. To this mixture was added dropwise 2.4 ml of Et$_3$N to dissolve all solid. To the cooled mixture at between 0 and 5° C. were added 0.9 ml of pivaloyl chloride and 30 mg of 4-dimethylaminopyridine (DMAP). The resulting mixture was stirred at between 0 and 5° C. for 18 hrs. The reaction mixture was poured into 10 ml of water. The layers were separated and the organic layer was washed with NaHCO$_3$ and water and concentrated under reduced pressure. The residue was chromatographed on a silica gel column, eluting with Hexane/EtOAc to give 1.56 g of 19a (81%). $^1$H NMR (CDCl$_3$) δ 7.45-7.31 (m, 6H), 6.28-6.18 (m, 1H), 5.81 (d, J=15.9 Hz, 1H), 5.62 (q, J=6.8 Hz, 1H), 5.20 (s, 2H), 4.78-4.68 (m, 1H), 3.88-3.70 (m, 2H), 2.52-2.15 (m, 4H), 1.57 (d, J=6.8 Hz, 3H).

Example 15

Preparation of Compound 18a

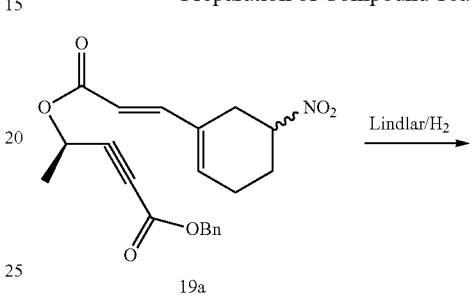
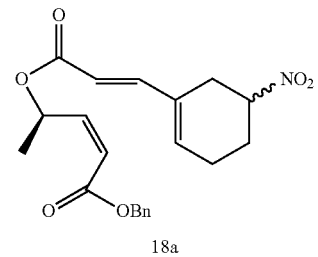

To a 100 ml Parr flask were added 1.4 g of 19a, 25 ml of toluene, 0.14 g of Lindlar catalyst (Alfa Chem), and 0.1 ml of quinoline. The flask was evacuated 3 times with nitrogen and vacuum and filled with hydrogen to 20 psi. The flask was shaken at room temperature for 3.5 hrs. The mixture was filtered through a pad of celite and washed with toluene. The filtrate was washed with 3×30 ml 1N HCl solution and 30 ml brine. The layers were separated and the organic layer was dried over MgSO$_4$ and concentrated to give 1.36 g (97%) of yellow oil. $^1$H NMR (CDCl$_3$) δ 7.45-7.10 (m, 7H), 6.41-6.31 (m, 1H), 6.28-6.15 (m, 2H), 5.90-5.78 (m, 2H), 5.18 (s, 2H), (m, 1H), 2.88-2.70 (m, 2H), 2.50-2.15 (m, 6H), 1.41 (d, J=6.5 Hz, 3H).

Example 16

Preparation of Compound 17a

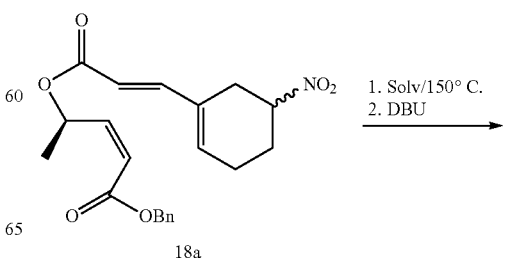

-continued

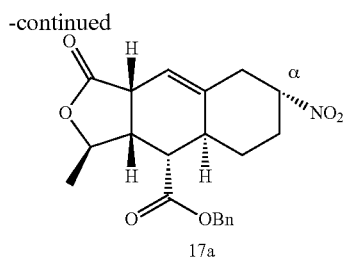
17a

To a flask were added 0.17 g of 18a and 3 ml of xylene. The mixture was heated to 150° C. for about 6 hrs and cooled to between 30 and 35° C. To the cooled mixture was added 1.5 ml of DBU. The resulting solution was heated at between 30 and 35° C. for 1 h to complete the epimerization of the initial trans product at the [6,5] junction to the cis product. There were a total of four isomers generated. The exo:endo ratio of the Diels-Alder reaction was about 78:22 and the α:β ratio was about 80:20. The solvent was removed under reduced pressure and the residue was purified on a silica gel column to give 0.082 g (48%) of the desired exo product and 0.025 g (15%) of the endo product. Exo-isomer (α:β mixture): $^1$NMR (CDCl$_3$) δ 7.45-7.32 (m, 5H), 5.51 (bs, 1H), 5.22-5.10 (m, 2H), 4.65 (bs, 1H, α-isomer), 4.46-4.30 (m, 2H), 3.37-3.30 (m, 1H), 3.14-3.09 (m, 1H, β-isomer), 2.94-2.89 (m, 1H), 2.75-1.75 (m, 7H), 1.12 (d, J=6.1 Hz, 3H, α-isomer), 1.11 (d, J=5.0 Hz, 3H, β-isomer). Endo-isomer $^1$H NMR (CDCl$_3$) δ 7.40-7.30 (m, 5H), 5.80 (bs, 1H), 5.25 (d, j=11.9 Hz, 1H), 4.60 (d, J=11.9 Hz, 1H), 4.58-4.48 (m, 1H), 4.15-4.05 (m, 1H), 3.35-3.25 (m, 1H), 3.06 (t, J=5.7 Hz, 1H), 2.95-2.88 (m, 1H), 2.65-2.50 (m, 2H), 2.40-2.30 (m, 1H), 2.28-2.20 (m, 1H), (m, 2H), 1.42 (d, J=6.5 Hz, 3H), 1.05-0.95 (m, 1H).

Example 17

Preparation of Compound 20

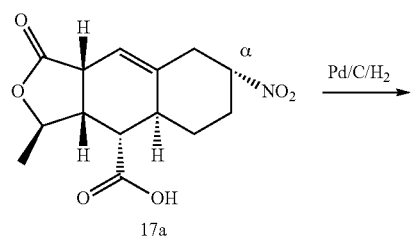
17a

Pd/C/H$_2$ →

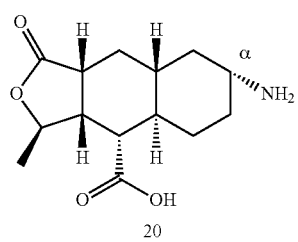
20

To a Parr flask were added 0.47 g of 17a, 35 ml of EtOAc, and 0.51 g of Pt/C. The flask was evacuated with nitrogen and vacuum 3 times, filled with hydrogen to 100 psi and was shaken for about 24 hrs as monitored by NMR. The mixture was filtered and washed with MeOH. The filtrate was concentrate to give 0.29 g of a gray solid. $^1$H NMR (Acetic acid-d$_4$) δ (α:β=78:22) 4.80-4.68 (m, 1H), 3.78 (bs, 1H, β-isomer), 3.41-3.28 (m, 1H, α-isomer), (m, 3H), 2.20-1.00 (m, 10H), 1.33 (d, J=5.8 Hz, 3H).

While the present invention has been described in conjunction with the specific embodiments set forth above, many alternatives, modifications and variations thereof will be apparent to those of ordinary skill in the art. All such alternatives, modifications, and variations are intended to fall within the spirit and scope of the present invention.

What is claimed is:

1. A process for preparing Compound 17:

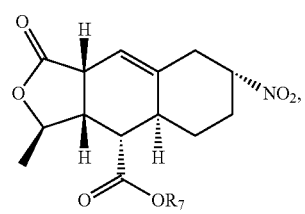
17 said process comprising the steps of:
(a) cyclizing Compound 18 in a first solvent at an elevated temperature

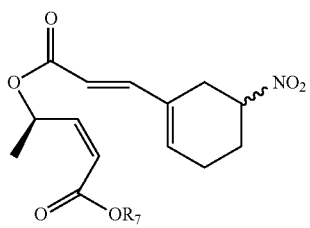
18 wherein R$_7$ is selected from the group consisting of H, alkyl, alkenyl, alkynyl, alkoxy, cycloalkyl, aryl, alkylaryl, arylalkyl, and heteroaryl groups
to produce a first mixture comprising α and β of the exo isomers of Compound 17A:

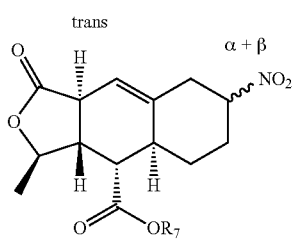
17A and α and β of the endo isomers of Compound 17B:

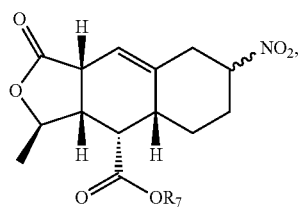

said isomers of Compound 17A having a trans-[5,6]-ring-junction;

(b) epimerizing said trans-[5,6]-ring-junction of Compound 17A by treating said first mixture with a first base to produce a second mixture comprising cis-[5,6]-ring-junction-nitro-α isomer and cis-[5,6]-ring-junction-nitro β isomer of each Compound 17C and Compound 17B:

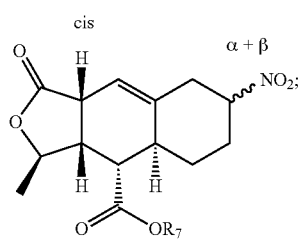

and (c) treating said second mixture with a second solvent, causing said α-isomer of Compound 17C to precipitate to produce Compound 17.

2. The process of claim 1 further comprising the step of treating said second mixture with a second base, resulting in a dynamic resolution of said second mixture, in which said β-isomer of Compound 17C is converted to α-isomer of Compound 17C, and α-isomer of Compound 17C is precipitated to produce Compound 17.

3. The process of claim 1, wherein said first solvent is selected from the group consisting of xylene, N-methylpyrrolidinone, Dimethylsulfoxide, diphenyl ether, and Dimethylacetamide, and mixtures of 2 or more thereof.

4. The process of claim 1, wherein said temperature is between about 70 and about 190° C.

5. The process of claim 1, wherein said temperature is between about 80 and about 170° C.

6. The process of claim 1, wherein said temperature is between about 100 and about 160° C.

7. The process of claim 1, wherein said temperature is between about 120 and about 150° C.

8. The process of claim 1, wherein said first base is selected from the group consisting of triethylamine; 1,5-diazabicyclo[4,3,0]non-5-ene 1,4-diazabicyclo[2,2,2]octane; and 1,8-diazabicyclo[5,4,0]undec-7-ene; and mixtures of 2 or more thereof.

9. The process of claim 1, wherein said second solvent is selected from the group consisting of alcohols, ethers, ketones, esters, xylene, and N-methylpyrrolidinone, and mixtures of 2 or more thereof.

10. The process of claim 1, wherein said second solvent is selected from the group consisting of methanol, ethanol, propanols, and butanols, xylene, N-methylpyrrolidinone, and mixtures of 2 or more thereof.

11. The process of claim 2, wherein said second base is selected from the group consisting of triethylamine; 1,5-diazabicyclo[4,3,0]non-5-ene 1,4-diazabicyclo[2,2,2]octane; 1,8-diazabicyclo[5,4,0]undec-7-ene; and mixtures of 2 or more thereof.

* * * * *